(12) United States Patent
Glenn, Jr. et al.

(10) Patent No.: US 8,476,211 B2
(45) Date of Patent: *Jul. 2, 2013

(54) POROUS, DISSOLVABLE SOLID SUBSTRATES AND SURFACE RESIDENT STARCH PERFUME COMPLEXES

(75) Inventors: Robert Wayne Glenn, Jr., Liberty Township, OH (US); Kathleen Mary Kaufman, Cincinnati, OH (US); Virginia Tzung-Hwei Hutchins, Cincinnati, OH (US); Zerlina Guzdar Dubois, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/561,298

(22) Filed: Jul. 30, 2012

(65) Prior Publication Data

US 2012/0289451 A1 Nov. 15, 2012

Related U.S. Application Data

(63) Continuation of application No. 12/633,335, filed on Dec. 8, 2009, now Pat. No. 8,268,764.

(60) Provisional application No. 61/120,786, filed on Dec. 8, 2008.

(51) Int. Cl.
| | | |
|---|---|---|
| C11D 11/00 | (2006.01) | |
| C11D 17/00 | (2006.01) | |
| C11D 3/22 | (2006.01) | |
| C11D 3/50 | (2006.01) | |
| A61K 8/73 | (2006.01) | |

(52) U.S. Cl.
USPC .......... 510/120; 510/130; 510/141; 510/441; 510/445; 510/474; 424/70.13

(58) Field of Classification Search
USPC 510/441, 445, 474, 120, 130, 141; 424/70.13
See application file for complete search history.

(56) References Cited

U.S. PATENT DOCUMENTS

| | | |
|---|---|---|
| 2,356,168 A | 8/1944 | Mabley |
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |

(Continued)

FOREIGN PATENT DOCUMENTS

| | | |
|---|---|---|
| CN | 1138091 A | 12/1996 |
| CN | 1219388 A | 6/1999 |

(Continued)

OTHER PUBLICATIONS

ISR dated May 6, 2011, PCT/US2009/067130, 5 pages.

(Continued)

*Primary Examiner* — Lorna M Douyon
(74) *Attorney, Agent, or Firm* — Angela K. Haughey

(57) ABSTRACT

The present invention relates to personal care compositions, especially those personal care compositions in the form of a personal care article that is a porous dissolvable solid substrate. The porous dissolvable solid substrate has a surface resident coating comprising the starch perfume complex that can provide a consumer benefit.

5 Claims, 4 Drawing Sheets

U.S. PATENT DOCUMENTS

| | | | |
|---|---|---|---|
| 2,528,378 A | 10/1950 | Mannheimer et al. | |
| 2,658,072 A | 11/1953 | Kosmin | |
| 2,694,668 A | 11/1954 | Fricke | |
| 2,809,971 A | 10/1957 | Bernstein et al. | |
| 3,152,046 A | 10/1964 | Kapral | |
| 3,236,733 A | 2/1966 | Karsten et al. | |
| 3,321,425 A | 5/1967 | Blau | |
| 3,332,880 A | 7/1967 | Kessler et al. | |
| 3,426,440 A | 2/1969 | Shen | |
| 3,489,688 A | 1/1970 | Pospischil | |
| 3,653,383 A | 4/1972 | Wise | |
| 3,695,989 A | 10/1972 | Albert | |
| 3,753,196 A | 8/1973 | Kurtz et al. | |
| 3,761,418 A | 9/1973 | Parran, Jr. | |
| 3,929,678 A | 12/1975 | Laughlin et al. | |
| 3,967,921 A | 7/1976 | Haberli | |
| 4,020,156 A | 4/1977 | Murray | |
| 4,051,081 A | 9/1977 | Jabs | |
| 4,089,945 A | 5/1978 | Brinkman et al. | |
| 4,196,190 A | 4/1980 | Gehman et al. | |
| 4,197,865 A | 4/1980 | Jacquet et al. | |
| 4,217,914 A | 8/1980 | Jacquet et al. | |
| 4,272,511 A | 6/1981 | Papantoniou et al. | |
| 4,323,683 A | 4/1982 | Bolich, Jr. et al. | |
| 4,345,080 A | 8/1982 | Bolich, Jr. | |
| 4,379,753 A | 4/1983 | Bolich, Jr. | |
| 4,381,919 A | 5/1983 | Jacquet et al. | |
| 4,422,853 A | 12/1983 | Jacquet et al. | |
| 4,470,982 A | 9/1984 | Winkler | |
| 4,507,280 A | 3/1985 | Pohl et al. | |
| 4,529,586 A | 7/1985 | De Marco et al. | |
| 4,565,647 A | 1/1986 | Llenado | |
| 4,663,158 A | 5/1987 | Wolfram et al. | |
| 4,710,374 A | 12/1987 | Grollier et al. | |
| 4,822,613 A | 4/1989 | Rodero | |
| 4,885,107 A | 12/1989 | Wetzel | |
| 4,976,953 A | 12/1990 | Orr et al. | |
| 4,990,280 A | 2/1991 | Thorengaard | |
| 5,055,384 A | 10/1991 | Kuhnert | |
| 5,061,481 A | 10/1991 | Suzuki et al. | |
| 5,062,889 A | 11/1991 | Hohl | |
| 5,094,853 A | 3/1992 | Hagerty | |
| 5,100,657 A | 3/1992 | Ansher-Jackson et al. | |
| 5,100,658 A | 3/1992 | Bolich, Jr. et al. | |
| 5,104,646 A | 4/1992 | Bolich, Jr. et al. | |
| 5,106,609 A | 4/1992 | Bolich, Jr. et al. | |
| 5,166,276 A | 11/1992 | Hayama et al. | |
| 5,220,033 A | 6/1993 | Kamei | |
| 5,280,079 A | 1/1994 | Allen et al. | |
| RE34,584 E | 4/1994 | Grote et al. | |
| 5,391,368 A | 2/1995 | Gerstein | |
| 5,409,703 A | 4/1995 | McAnalley et al. | |
| 5,429,628 A | 7/1995 | Trinh et al. | |
| 5,457,895 A | 10/1995 | Thompson | |
| 5,476,597 A | 12/1995 | Sakata | |
| 5,580,481 A | 12/1996 | Sakata | |
| 5,582,786 A | 12/1996 | Brunskill et al. | |
| 5,660,845 A | 8/1997 | Trinh et al. | |
| 5,672,576 A | 9/1997 | Behrens et al. | |
| 5,674,478 A | 10/1997 | Dodd et al. | |
| 5,750,122 A | 5/1998 | Evans et al. | |
| 5,780,047 A | 7/1998 | Kamiya | |
| 5,955,419 A | 9/1999 | Barket, Jr. et al. | |
| 6,010,719 A | 1/2000 | Remon | |
| 6,106,849 A | 8/2000 | Malkan et al. | |
| 6,177,391 B1 | 1/2001 | Zafar | |
| 6,200,949 B1 | 3/2001 | Reijmer | |
| 6,458,754 B1 | 10/2002 | Velaquez et al. | |
| 6,503,521 B1 | 1/2003 | Atis | |
| 6,790,814 B1 | 9/2004 | Marin et al. | |
| 6,846,784 B2 | 1/2005 | Engel | |
| 6,943,200 B1 | 9/2005 | Corrand et al. | |
| 7,015,181 B2 | 3/2006 | Lambino | |
| 7,285,520 B2 | 10/2007 | Krzysik | |
| 7,901,696 B2 | 3/2011 | Eknoian et al. | |
| 8,268,764 B2 * | 9/2012 | Glenn et al. | 510/120 |
| 2002/0064510 A1 | 5/2002 | Dalrymple et al. | |
| 2002/0077264 A1 | 6/2002 | Roberts | |
| 2002/0081930 A1 | 6/2002 | Jackson | |
| 2002/0098994 A1 | 7/2002 | Zafar | |
| 2002/0099109 A1 | 7/2002 | Dufton | |
| 2002/0177621 A1 | 11/2002 | Hanada | |
| 2002/0187181 A1 | 12/2002 | Godbey | |
| 2003/0032573 A1 | 2/2003 | Tanner | |
| 2003/0045441 A1 | 3/2003 | Hsu | |
| 2003/0069154 A1 | 4/2003 | Hsu | |
| 2003/0080150 A1 | 5/2003 | Cowan | |
| 2003/0099691 A1 | 5/2003 | Lydzinski | |
| 2003/0099692 A1 | 5/2003 | Lydzinski | |
| 2003/0180242 A1 | 9/2003 | Eccard | |
| 2003/0186826 A1 | 10/2003 | Eccard | |
| 2003/0194416 A1 | 10/2003 | Shefer | |
| 2003/0199412 A1 | 10/2003 | Gupta | |
| 2003/0207776 A1 | 11/2003 | Shefer | |
| 2003/0215522 A1 | 11/2003 | Johnson et al. | |
| 2003/0232183 A1 | 12/2003 | Dufton | |
| 2004/0029762 A1 | 2/2004 | Hensley | |
| 2004/0032859 A1 | 2/2004 | Mino | |
| 2004/0048759 A1 | 3/2004 | Ribble et al. | |
| 2004/0053808 A1 | 3/2004 | Raehse | |
| 2004/0071742 A1 | 4/2004 | Popplewell | |
| 2004/0071755 A1 | 4/2004 | Fox | |
| 2004/0108615 A1 | 6/2004 | Foley | |
| 2004/0110656 A1 | 6/2004 | Casey | |
| 2004/0126585 A1 | 7/2004 | Kerins | |
| 2004/0175404 A1 | 9/2004 | Shefer | |
| 2004/0202632 A1 | 10/2004 | Gott et al. | |
| 2004/0206270 A1 | 10/2004 | Vanmaele et al. | |
| 2004/0242772 A1 | 12/2004 | Huth | |
| 2005/0069575 A1 | 3/2005 | Fox | |
| 2005/0136780 A1 | 6/2005 | Clark | |
| 2005/0137272 A1 | 6/2005 | Gaserod | |
| 2005/0202992 A1 | 9/2005 | Grandio Portabales | |
| 2005/0220745 A1 | 10/2005 | Lu | |
| 2005/0232954 A1 | 10/2005 | Yoshinari et al. | |
| 2005/0272836 A1 | 12/2005 | Yaginuma | |
| 2005/0287106 A1 | 12/2005 | Legendre | |
| 2006/0002880 A1 | 1/2006 | Peffly et al. | |
| 2006/0052263 A1 | 3/2006 | Roreger | |
| 2006/0228319 A1 | 10/2006 | Vona | |
| 2007/0028939 A1 | 2/2007 | Mareri | |
| 2007/0149435 A1 | 6/2007 | Koenig | |
| 2007/0225388 A1 | 9/2007 | Cooper et al. | |
| 2008/0035174 A1 | 2/2008 | Aubrun-Sonneville | |
| 2008/0090939 A1 | 4/2008 | Netravali | |
| 2008/0131695 A1 | 6/2008 | Aouad | |
| 2008/0138492 A1 | 6/2008 | Cingotti | |
| 2008/0152894 A1 | 6/2008 | Beihoffer et al. | |
| 2008/0215023 A1 | 9/2008 | Scavone et al. | |
| 2008/0293839 A1 | 11/2008 | Stobby | |
| 2009/0232873 A1 | 9/2009 | Glenn, Jr. | |
| 2009/0263342 A1 | 10/2009 | Glenn, Jr. | |
| 2010/0167971 A1 | 7/2010 | Glenn, Jr. | |
| 2010/0173817 A1 | 7/2010 | Glenn, Jr. | |
| 2010/0179083 A1 | 7/2010 | Glenn, Jr. | |
| 2010/0279905 A1 | 11/2010 | Glenn, Jr. | |
| 2010/0286011 A1 | 11/2010 | Glenn, Jr. | |
| 2010/0291165 A1 | 11/2010 | Glenn, Jr. | |
| 2010/0298188 A1 | 11/2010 | Glenn, Jr. | |
| 2011/0023240 A1 | 2/2011 | Fossum | |
| 2011/0028373 A1 | 2/2011 | Fossum | |
| 2011/0028374 A1 | 2/2011 | Fossum | |
| 2011/0182956 A1 | 7/2011 | Glenn, Jr. | |
| 2011/0189246 A1 | 8/2011 | Glenn, Jr. | |
| 2011/0189247 A1 | 8/2011 | Glenn, Jr. | |
| 2011/0195098 A1 | 8/2011 | Glenn, Jr. | |
| 2012/0021026 A1 | 1/2012 | Chhabra | |

FOREIGN PATENT DOCUMENTS

| | | | |
|---|---|---|---|
| CN | 1268558 A | 10/2000 | |
| CN | 1357613 A | 7/2002 | |
| CN | 1530431 A | 9/2004 | |
| CN | 1583991 A | 2/2005 | |
| DE | 19607851 A1 | 9/1997 | |
| DE | 10331767 A1 | 2/2005 | |
| EP | 609808 A1 | 8/1994 | |
| EP | 0858828 A1 | 8/1998 | |

| | | | |
|---|---|---|---|
| EP | 1160311 B1 | 12/2001 | |
| EP | 1217987 B1 | 12/2004 | |
| EP | 2085434 A1 | 8/2009 | |
| FR | 2871685 A | 12/2005 | |
| FR | 2886845 A | 12/2006 | |
| GB | 2235204 A | 2/1991 | |
| GB | 2355008 A | 4/2001 | |
| JP | 58021608 A | 2/1983 | |
| JP | 58216109 A | 12/1983 | |
| JP | 62072609 A | 4/1987 | |
| JP | 62072610 A | 4/1987 | |
| JP | 1313418 A | 12/1989 | |
| JP | 5344873 A | 12/1993 | |
| JP | 6017083 A | 1/1994 | |
| JP | 7089852 A | 4/1995 | |
| JP | 8325133 A | 12/1996 | |
| JP | 10251371 A | 9/1998 | |
| JP | 2003073700 A | 3/2003 | |
| JP | 2003082397 A | 3/2003 | |
| JP | 2004345983 A | 12/2004 | |
| JP | 2005171063 A | 6/2005 | |
| JP | 2007197540 A | 8/2007 | |
| JP | 2007091954 A | 12/2007 | |
| KR | 20020003442 | 1/2002 | |
| WO | WO9514495 A1 | 6/1995 | |
| WO | WO01/24770 A1 | 4/2001 | |
| WO | WO 2004/032859 A | 4/2004 | |
| WO | WO2004/041991 A1 | 5/2004 | |
| WO | WO2005/003423 A1 | 1/2005 | |
| WO | WO2007033598 A1 | 3/2007 | |
| WO | WO2007093558 A2 | 8/2007 | |
| WO | WO2009019571 | 2/2009 | |

OTHER PUBLICATIONS

ISR dated May 4, 2011, PCT/US2009/067088, 5 pages.
ISR dated Jul. 19, 2011, PCT/US2009/067088, 7 pages.
ISR dated May 9, 2011, PCT/US2009/067132, 5 pages.
ISR dated Apr. 29, 2011, PCT/US2009/067089, 5 pages.
ISR dated Jul. 15, 2009, PCT/IB2009/050388, 8 pages.
ISR dated Aug. 17, 2009, PCT/US2009/040739, 6 pages.
ISR dated Nov. 4, 2009, PCT/US2009/040739, 10 pages.
ISR dated Dec. 15, 2011, PCT/US2009/067087, 5 pages.
ISR dated Jul. 19, 2011, PCT/US2009/067133, 4 pages.
ISR dated Jul. 19, 2011, PCT/US2009/067130, 7 pages.
ISR dated Apr. 27, 2011, PCT/US2010/059365, 5 pages.
ISR dated Apr. 27, 2011, PCT/US2010/059455, 5 pages.
ISR dated Apr. 27, 2011, PCT/US2010/059359, 5 pages.
Anonymous: "P8136 Poly(vinyl alcohol)" Internet article, [Online] XP002538935 Retrieved from the Internet: URL:http://www.sigmaaldrich.com/catalog/ProductDetail.do?D7=0&N25=SEARCH_CONCAT_PNO%7CBRAND_KEY&N4=P8136%7CSIAL&N25=0&QS=0N&F=SPEC> [retrieved on Jul. 28, 2009].
M. K. Industires (Gujarat India, http://www.soapstrips.com).
Sanipro Sanitary Products (Italy, http://www.sanipro.it).
Adhesives Research (Pennsylvania, http://12.4.33.51/news/apresmed.htm).
Solublon (Toyohashi Japan, http://www.solublon.com).
SPI Pharma (Delaware, http://www.spipharma.com).
Wenda (China, http://www.wenda.com).
MOVA Pharmaceutical and Kosmos (USA, http://www.icon-pr.com/news/news_print.cfm?inv_id=266-1).
Cima Labs, Inc. (Minnesota, http://www.cimalabs.com/).
Cardinal Health (Dublin, Ohio, http://spd.cardinal.com/).
Le Laboratoire du Bain (France, http://www.laboduain.com/).
Amerilab Technologies, Inc. (Minnesota, http://www.amerilabtech.com/).
Meguiar's Car Wash Strips: (Meguiar's Inc. California, http://www.automotivedigest.com/view_art.asp?articlesID=12414).
Pure Soap Leafz: (Soap UNLTD, Netherlands, http://www.upandunder.co.uk/eshop/catalogue/testbs.asp?Manufacturer_ID=252&Activity_ID=33&Description_ID=157).
Dissolving Soap Strips (Ranir LLC, Michigan, www.ranir.com).
Japanese Paper Soap (http://www.wishingfish.com/papersoap.html).
Travelers Passport Paper Soap Sheets (http://www.weddingfavorsnow.com/index.asp?PageAction=VIEWPROD&ProdID=510).
Office Action for U.S. Appl. No. 12/424,812 dated Nov. 1, 2011; Glenn, Jr. et al.; filed Apr. 16, 2009.
Office Action for U.S. Appl. No. 12/633,228 dated May 11, 2011; Glenn, Jr. et al.; filed Dec. 8, 2009.
Office Action for U.S. Appl. No. 12/633,228 dated Oct. 25, 2011; Glenn, Jr. et al.; filed Dec. 8, 2009.
Office Action for U.S. Appl. No. 12/633,257 dated Jun. 1, 2011; Glenn, Jr. et al.; filed Dec. 8, 2009.
Office Action for U.S. Appl. No. 12/633,257 dated Nov. 17, 2011; Glenn, Jr. et al.; filed Dec. 8, 2009.
Office Action for U.S. Appl. No. 12/633,301 dated Jun. 3, 2011; Glenn, Jr. et al.; filed Dec. 8, 2009.
Office Action for U.S. Appl. No. 12/633,301 dated Nov. 7, 2011; Glenn, Jr. et al.; filed Dec. 8, 2009.
Office Action for U.S. Appl. No. 12/633,335 dated Jul. 8, 2011; Glenn, Jr. et al.; filed Dec. 8, 2009.
Office Action for U.S. Appl. No. 12/633,415 dated Nov. 14, 2011; Glenn, Jr. et al.; filed Dec. 8, 2009.
Office Action for U.S. Appl. No. 12/633,572 dated Jul. 28, 2011; Glenn, Jr. et al.; filed Dec. 8, 2009.
Office Action for U.S. Appl. No. 12/361,634 dated Sep. 14, 2011; Glenn, Jr. et al.; filed Jan. 29, 2009.
International Search Report, dated Jul. 20, 2011, PCT/US2009/067131.
T. Hildebrand, P. Rüegsegger. "Quantification of bone microarchitecture with the structure model index." Computer Methods in Biomechanics and Biomedical Engineering 1997; 1:15-23.
Vesterby, A.; Star volume in bone research. A histomorphometric analysis of trabecular bone structure using vertical sections; Anat Rec.; Feb. 1993; 235(2): 325-334.
C. D. Vaughan. Solubility, Effects in Product, Package, Penetration and Preservation, Cosmetics and Toiletries, vol. 103, Oct. 1988.
*Encyclopedia of Polymer Science and Engineering*, vol. 15, 2d ed., pp. 204-308, John Wiley & Sons, Inc. (1989).
U.S. Appl. No. 13/440,475, filed Apr. 5, 2012, Granberg et al.

* cited by examiner

POROUS, DISSOLVABLE SOLID SUBSTRATES AND SURFACE RESIDENT STARCH PERFUME COMPLEXES

CROSS REFERENCE TO RELATE APPLICATION

This application is a continuation of U.S. application Ser. No. 12/633,335, filed on Dec. 8, 2009, now U.S. Pat. No. 8,268,764, which claims the benefit of U.S. Provisional Application Ser. No. 61/120,786, filed on Dec. 8, 2008 which is incorporate by reference herein.

FIELD OF THE INVENTION

The present invention relates to personal care compositions, especially those personal care compositions providing personal care benefits in the form of an article comprising a porous dissolvable solid substrate and surface resident starch perfume complexes.

BACKGROUND OF THE INVENTION

Personal care compositions have traditionally been sold as liquid products. These liquid personal care products typically comprise a substantial amount of water in the formula. In addition to being liquids, many of the personal care products contain perfumes, as consumers typically desire perfumed personal care products. However, due to the water present in the personal care products, inclusion of perfume is limited to either the solubilization or emulsification within aqueous amphiphile assemblies (micelles, liquid crystals etc.). As a result, a significant portion of the perfume molecules are "trapped" within these aqueous assemblies which can limit the efficient delivery of the perfume to the nostrils of the consumer during product usage (i.e. lower perfume bloom) and to the target keratinous substrate (i.e. skin and hair). Moreover, choice of perfume is limited to those that deliver a single scent experience to the consumer (i.e. the scent of the product as packaged is the same and the only perfume experienced during use), and precludes delivery of a perfume that is activated by water during use.

Thus it is an object of the invention to provide a personal care product that can more efficiently deliver perfumes during consumer usage. It is also an object of the invention to provide a personal care product that delivers a perfume that can be water activated, i.e., the release of the perfume being maximally triggered via the addition of water to the product during usage. It is additionally an object of the invention to provide a personal care product that can deliver not only a primary perfume, but a secondary perfume that results in a second burst of perfume that is activated by water during use. For example the personal care product can have one perfume prior to being combined with water, and after exposure to water the personal care product can have a second perfume and/or a perfume bloom of the same original perfume.

SUMMARY OF THE INVENTION

The present invention meets the aforementioned needs. The present invention provides a porous dissolvable solid substrate in the form of a unit dose personal care article that can be conveniently and quickly dissolved in the palm of the consumer's hand to reconstitute a liquid personal care composition for ease of application to hair while providing the consumer desired perfumes both before and during use.

A personal care article comprising: (i) a porous dissolvable solid substrate comprising: from about 10% to about 75% of a surfactant; from about 10% to about 50% water-soluble polymer; from about 1% to about 30% plasticizer; and (ii) a surface resident coating comprising from about 10% to about 100% of one or more starch perfume complexes; wherein the ratio of the starch to perfume in the complex is from about 0.5:1 to about 19:1, and wherein the ratio of the porous dissolvable solid substrate to the surface resident coating is from 110:1 to about 0.5:1.

A method for making a personal care article, the method comprising applying a surface resident coating comprising the starch perfume complex in powdered form to a porous dissolvable solid substrate comprising from about 10% to about 75% of a surfactant, from about 10% to about 50% water-soluble polymer, and from about 1% to about 30% plasticizer.

A method for making a personal care article, the method comprising: preparing a processing mixture comprising from about 5% to about 50% of a surfactant, from about 5% to about 35% water-soluble polymer, and from about 0.5% to about 20% plasticizer; aerating the processing mixture by introducing a gas into the processing mixture to form an aerated wet mixture; forming the aerated wet mixture into one or more desired shapes; drying the aerated wet mixture to form a porous dissolvable solid substrate; and applying a surface resident coating comprising the starch perfume complex in powdered form to the porous dissolvable solid substrate.

BRIEF DESCRIPTION OF THE DRAWINGS

While the specification concludes with claims which particularly point out and distinctly claim the present invention, it is believed that the present invention will be better understood from the following description of embodiments, taken in conjunction with the accompanying drawings, in which like reference numerals identify identical elements and wherein:

DETAILED DESCRIPTION OF THE INVENTION

Figure 1:
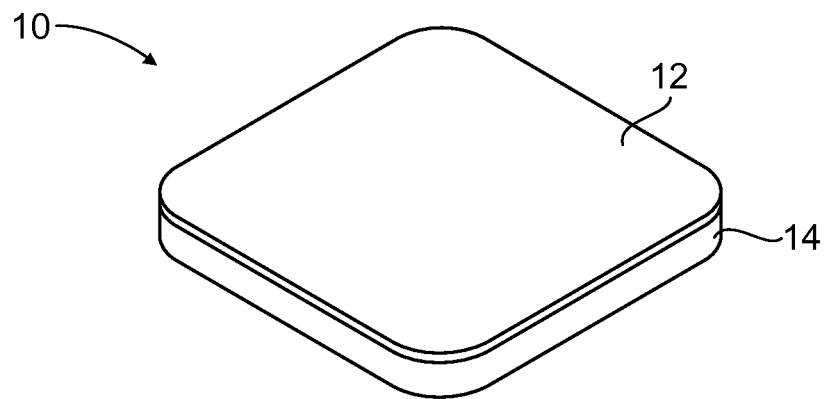
FIG. 1 is a schematic view of a porous dissolvable solid substrate with a surface resident starch perfume complex.

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

I. DEFINITIONS

As used herein, the term "personal care composition" means a composition that may be applied to mammalian hair and skin without undue undesirable effects.

As used herein, the term "starch perfume complexes" refers to a perfume complexed within water-releasable matrices comprised of starch or modified starch in particulate form.

The term, "surface resident starch perfume complex," as used herein, refers to a surface resident coating comprising a starch perfume complex that is adsorbed to at least a portion of the solid/air interface of the porous dissolvable solid substrate. The resulting surface resident coating minimizes the physical interactions between the starch perfume complex and the bulk of the dissolvable porous solid over the shelf life of the product, and before the personal care article is put in contact with water during consumer use.

As used herein, "personal care article" means the porous dissolvable solid substrate comprising a surfactant, water-soluble polymer, and plasticizer, along with the surface resident coating of the starch perfume complex. The personal care article may be referred to herein as "the article."

As used herein, "dissolvable" means that the porous dissolvable solid substrate has a dissolution rate that satisfies the Hand Dissolution Method Test described herein.

As used herein "porous dissolvable solid substrate" means a solid polymer-containing matrix that defines an interconnected network of spaces or cells that contain the gas of the surrounding atmosphere, typically air. The interconnectivity of the structure may be described by a Star Volume, a Structure Model Index (SMI) or a Percent Open Cell Content.

II. PERSONAL CARE ARTICLE

The personal care article of the present invention delivers a unique perfume experience to the consumer from a lathering/cleansing product by enabling the more efficient delivery of perfumes as well as the water activated release of a perfume during consumer usage. The water activated perfume may encompass a secondary perfume such that the personal care product can have one perfume prior to being combined with water, and after exposure to water the personal care product can have a second perfume and/or a perfume bloom of the same original perfume.

This is achieved by incorporating a surface resident coating comprising a starch perfume complex on the porous dissolvable solid substrate. Any suitable application method can be used to apply the surface resident coating comprising the starch perfume complex to the porous dissolvable solid substrate to form a surface resident coating that is adsorbed to at least a portion of the solid/air interface of the porous dissolvable solid substrate. In a one embodiment surface resident coating comprising the starch perfume complex is in the form of a powder coating, which is applied to the surface of the porous dissolvable solid substrate.

Traditionally, perfumes are delivered from aqueous liquid consumer products via the solubilization or emulsification of the perfume within stabilized aqueous amphiphile assemblies (e.g., micelles, liquid crystals etc.). This may result in the less efficient delivery of the perfume to the nostrils of the consumer during product usage (i.e. lower perfume bloom) and to the target keratinous substrate (i.e., skin and hair). This may be due to the "entrapment" of the perfume molecules within the stabilized aqueous amphiphile assemblies which may hinder the diffusion of the hydrophobic perfume molecules through the aqueous phase to the water/air and water/substrate interfaces during product usage, thereby reducing the efficient delivery of the perfume molecules to the intended targets (consumer nostrils and keratinous substrates) and even resulting in greater amounts of the perfume molecules being wasted ("rinsed down the drain"). While this may still occur in the present inventive personal care articles as they are dissolved in water immediately prior to application to the hair or skin, such physical "entrapment" interactions are minimized when the personal care articles are made and/or used according to the present invention.

The present invention also enables the delivery of a perfume that is activated by water, i.e., the release of the perfume being maximally triggered via the addition of water to the product during usage. This occurs due to the starch perfume complexes of the present invention being water releasable, i.e., the starch dissolves with the perfume physically released or liberated as the personal care article is dissolved in water.

This present invention additionally enables the unique and optional delivery of both a primary perfume and a secondary perfume during the product usage experience by the consumer. For example the personal care product can have one perfume prior to being combined with water, and after exposure to water the personal care product can have a second perfume and/or a more intense perfume bloom of the same original perfume. This can be achieved by incorporating a secondary perfume within the starch perfume complex with a perfume distinct from the primary perfume. Alternatively, a the same perfume may be employed within the starch perfume complex, but enabling a more intense perfume bloom upon the dissolution of the personal care article.

A. The Porous Dissolvable Solid Substrate

The porous dissolvable solid substrate comprises a surfactant, a water-soluble polymer, and a plasticizer. The porous dissolvable solid substrate can be prepared such that it can be conveniently and quickly dissolved in the palm of the consumer resulting in a liquid personal care composition. Once dissolved, this personal care composition can be used in a manner similar to conventional liquid personal care compositions, i.e. applied to the scalp and/or hair. The porous dissolvable solid substrate has a maximum Cell Wall Thickness. The porous dissolvable solid substrate has a Cell Wall Thickness of from about from about 0.02 mm to about 0.15 mm, in one embodiment from about 0.025 mm to about 0.12 mm, in another embodiment from about 0.03 mm to about 0.09 mm, and in still another embodiment from about 0.035 mm to about 0.06 mm. The porous dissolvable solid substrate has a minimum level of interconnectivity between the cells, which is quantified by the Star Volume, the Structure Model Index (SMI), and the Percent Open Cell Content. The porous dissolvable solid substrate has a Star Volume of from about 1 $mm^3$ to about 90 $mm^3$, in one embodiment from about 1.5 $mm^3$ to about 60 $mm^3$, in another embodiment from about 2 $mm^3$ to about 30 $mm^3$, and in still another embodiment from about 2.5 $mm^3$ to about 15 $mm^3$. The porous dissolvable solid substrate has a non-negative Structure Model Index of from about 0.0 to about 3.0, in one embodiment from about 0.5 to about 2.75, and in another embodiment from about 1.0 to about 2.50. The porous dissolvable solid substrate has a Percent Open Cell Content of from about 80% to 100%, in one embodiment from about 85% to about 97.5%, and in another embodiment from about 90% to about 95%. The porous dissolvable solid substrate also has a minimum Specific Surface Area. The porous dissolvable solid substrate has a Specific Surface Area of from about 0.03 m$^2$/g to about 0.25 m$^2$/g, in one embodiment from about 0.035 m$^2$/g to about 0.22 m$^2$/g, in another embodiment from about 0.04 m$^2$/g to about 0.19 m$^2$/g, and in still another embodiment from about 0.045 m$^2$/g to about 0.16 m$^2$/g. The porous dissolvable solid substrate has a basis weight of from about 125 grams/m$^2$ to about 3,000 grams/m$^2$, in one embodiment from about 300 grams/m$^2$ to about 2,500 grams/m$^2$, in another embodiment from about 400 grams/m$^2$ to about 2,000 grams/m$^2$, in another embodiment from about 500 grams/m$^2$ to about 1,500 grams/m$^2$ and in another embodiment from about 600 grams/m$^2$ to about 1,200 grams/m$^2$, and in another embodiment from about 700 to about 1,000 grams/m$^2$ The porous dissolvable solid substrate has a solid density of from about 0.03 g/cm$^3$ to about 0.40 g/cm$^3$, in one embodiment from about 0.05 g/cm$^3$ to about 0.35 g/cm$^3$, in another embodiment from about 0.08 g/cm$^3$ to about 0.30 g/cm$^3$, in another embodiment from about 0.10 g/cm$^3$ to about 0.25 g/cm$^3$, and in another embodiment from about 0.12 g/cm$^3$ to about 0.20 g/cm$^3$.

In one embodiment, the porous dissolvable solid substrate of present invention is a flat, flexible substrate in the form of a pad, a strip or tape and having a thickness of from about 0.5 mm to about 10 mm, in one embodiment from about 1 mm to about 9 mm, in another embodiment from about 2 mm to about 8 mm, and in a further embodiment from about 3 mm to about 7 mm as measured by the below methodology.

1. Surfactants

The porous dissolvable solid substrates of the present invention may be lathering or non-lathering under consumer relevant usage instructions. The porous dissolvable substrates include at least one surfactant as a processing aid to generate a stable foam solid prior to drying (solidification) and in the case of a lathering substrate the surfactant may also serve dual functions as a foaming and/or cleansing agent.

a. Lathering Porous Dissolvable Solid Substrates

Lathering porous dissolvable solid substrates for the purposes of lathering and/or cleaning comprise from about 10% to about 75%, in one embodiment from about 30% to about 70%, and in another embodiment from about 40% to about 65% by weight of the personal care article of surfactant; wherein the surfactant comprises one or more surfactants from Group I, wherein Group I includes anionic surfactants which are suitable for use in hair care or other personal care compositions, and optionally one or more surfactants from Group II, wherein Group II includes a surfactant selected from the group consisting of amphoteric, zwitterionic and combinations thereof suitable for use in hair care or other personal care compositions; wherein the ratio of Group I to Group II surfactants is from about 100:0 to about 30:70. In another embodiment of the present invention the ratio of Group I to Group II surfactants is from about 85:15 to about 40:60. In yet another embodiment of the present invention the ratio of Group I to Group II surfactants is from about 70:30 to about 55:45.

Non limiting examples of anionic surfactants are described in U.S. Pat. Nos. 2,486,921; 2,486,922; and 2,396,278. The anionic surfactant can be selected from the group consisting of alkyl and alkyl ether sulfates, sulfated monoglycerides, sulfonated olefins, alkyl aryl sulfonates, primary or secondary alkane sulfonates, alkyl sulfosuccinates, acid taurates, acid isethionates, alkyl glycerylether sulfonate, sulfonated methyl esters, sulfonated fatty acids, alkyl phosphates, acyl glutamates, acyl sarcosinates, alkyl lactylates, anionic fluorosurfactants, sodium lauroyl glutamate, and combinations thereof.

Non limiting examples of suitable zwitterionic or amphoteric surfactants are described in U.S. Pat. Nos. 5,104,646 (Bolich Jr. et al.), 5,106,609 (Bolich Jr. et al.).

Additional suitable Group I and Group II surfactants include those disclosed in U.S. Patent Application No. 61/120,765 and those surfactants disclosed in McCutcheon's Detergents and Emulsifiers, North American Edition (1986), Allured Publishing Corp.; McCutcheon's, Functional Materials, North American Edition (1992), Allured Publishing Corp.; and U.S. Pat. No. 3,929,678 (Laughlin et al.). Other non-limiting examples of suitable surfactants are included in U.S. Ser. No. 61/120,790.

b. Non-Lathering Porous Dissolvable Solid Substrates

The non-lathering porous dissolvable solid substrates comprise from about 10% to about 75%, in another embodiment from about 15% to about 60%, and in another embodiment from about 20% to about 50% by weight of the personal care article of surfactant; wherein the surfactant comprises one or more of the surfactants described below.

(i) Anionic Surfactants

If the porous dissolvable solid substrate of the present invention is non lathering, the substrate may comprise a maximum level of 10% (or less than 10%) of anionic surfactants to be used primarily as a process aid in making a stable foam solid.

(ii) Non-Ionic Surfactants

In one embodiment non-ionic surfactants are included as a process aid in making a stable porous dissolvable solid substrate. Suitable nonionic surfactants for use in the present invention include those described in McCutcheon's Detergents and Emulsifiers, North American edition (1986), Allured Publishing Corp., and McCutcheon's Functional Materials, North American edition (1992). Suitable nonionic surfactants for use in the personal care compositions of the present invention include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

(iii) Polymeric Surfactants

Polymeric surfactants can also be surfactants to be employed as a process aid in making the porous dissolvable solid substrate of the present invention, either alone or in combination with ionic and/or nonionic surfactants. Suitable polymeric surfactants for use in the personal care compositions of the present invention include, but are not limited to, block copolymers of ethylene oxide and fatty alkyl residues, block copolymers of ethylene oxide and propylene oxide, hydrophobically modified polyacrylates, hydrophobically modified celluloses, silicone polyethers, silicone copolyol esters, diquaternary polydimethylsiloxanes, and co-modified amino/polyether silicones.

2. Water-Soluble Polymer ("Polymer Structurant")

The porous dissolvable solid substrate comprises water-soluble polymers that function as a structurant. As used herein, the term "water-soluble polymer" is broad enough to include both water-soluble and water-dispersible polymers, and is defined as a polymer with a solubility in water, measured at 25° C., of at least about 0.1 gram/liter (g/L). In some embodiments, the polymers have solubility in water, measured at 25° C., of from about 0.1 gram/liter (g/L), to about 500 grams/liter (g/L). (This indicates production of a macroscopically isotropic or transparent, colored or colorless solution). The polymers for making these solids may be of synthetic or natural origin and may be modified by means of chemical reactions. They may or may not be film-forming. These polymers should be physiologically acceptable, i.e., they should be compatible with the skin, mucous membranes, the hair and the scalp.

The one or more water-soluble polymers may be present from about 10% to about 50% by weight of the porous dissolvable solid substrate, in one embodiment from about 15% to about 40% by weight of the porous dissolvable solid substrate, and in yet another embodiment from about 20% to about 30% by weight of the porous dissolvable solid substrate.

The one or more water-soluble polymers of the present invention are selected such that their weighted average molecular weight is from about 40,000 to about 500,000, in one embodiment from about 50,000 to about 400,000, in yet another embodiment from about 60,000 to about 300,000, and in still another embodiment from about 70,000 to about 200,000. The weighted average molecular weight is computed by summing the average molecular weights of each polymer raw material multiplied by their respective relative weight percentages by weight of the total weight of polymers present within the porous dissolvable solid substrate.

In one embodiment, at least one of the one or more water-soluble polymers is chosen such that about 2% by weight solution of the water-soluble polymer gives a viscosity at 20° C. of from about 4 centipoise to about 80 centipoise; in an alternate embodiment from about 5 centipoise to about 70 centipoise; and in another embodiment from about 6 centipoise to about 60 centipoise.

The water-soluble polymer(s) of the present invention can include, but are not limited to, synthetic polymers as described in U.S. Ser. No. 61/120,786 including polymers derived from acrylic monomers such as the ethylenically unsaturated carboxylic monomers and ethylenically unsaturated monomers as described in U.S. Pat. No. 5,582,786 and EP-A-397410. The water-soluble polymer(s) which are suitable may also be selected from naturally sourced polymers including those of plant origin examples which are described in U.S. Ser. No. 61/120,786. Modified natural polymers are also useful as water-soluble polymer(s) in the present invention and are included in U.S. Ser. No. 61/120,786. In one embodiment, water-soluble polymers of the present invention include polyvinyl alcohols, polyacrylates, polymethacrylates, copolymers of acrylic acid and methyl acrylate, polyvinylpyrrolidones, polyalkylene oxides, starch and starch derivatives, pullulan, gelatin, hydroxypropylmethylcelluloses, methylcelluloses, and carboxymethycelluloses. In another embodiment, water-soluble polymers of the present invention include polyvinyl alcohols, and hydroxypropylmethylcelluloses. Suitable polyvinyl alcohols include those available from Celanese Corporation (Dallas, Tex.) under the CELVOL® trade name. Suitable hydroxypropylmethylcelluloses include those available from the Dow Chemical Company (Midland, Mich.) under the METHOCEL® trade name.

In a particular embodiment, the above mentioned water-soluble polymer(s) may be blended with any single starch or combination of starches as a filler material in such an amount as to reduce the overall level of water-soluble polymers required, so long as it helps provide the personal care article with the requisite structure and physical/chemical characteristics as described herein.

In such instances, the combined weight percentage of the water-soluble polymer(s) and starch-based material generally ranges from about 10% to about 50%, in one embodiment from about 15% to about 40%, and in a particular embodiment from about 20% to about 30% by weight relative to the total weight of the porous dissolvable solid substrate. The weight ratio of the water-soluble polymer(s) to the starch-based material can generally range from about 1:10 to about 10:1, in one embodiment from about 1:8 to about 8:1, in still another embodiment from about 1:7 to about 7:1, and in yet another embodiment from about 6:1 to about 1:6.

Typical sources for starch-based materials can include cereals, tubers, roots, legumes and fruits. Native sources can include corn, pea, potato, banana, barley, wheat, rice, sago, amaranth, tapioca, arrowroot, canna, sorghum, and waxy or high amylase varieties thereof. The starch-based materials may also include native starches that are modified using any modification known in the art, including those described in U.S. Ser. No. 61/120,786.

3. Plasticizer

The porous dissolvable solid substrate of the present invention comprises a water soluble plasticizing agent suitable for use in personal care compositions. In one embodiment, the one or more plasticizers may be present from about 1% to about 30% by weight of the porous dissolvable solid substrate; in another embodiment from about 3% to about 25%; in another embodiment from about 5% to about 20%, and in yet another embodiment, from about 8% to about 15%. Non-limiting examples of suitable plasticizing agents include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, and high fructose corn syrup solids and ascorbic acid. Suitable examples of polycarboxylic acids for use herein are disclosed in U.S. Ser. No. 61/120,786.

In one embodiment, the plasticizers include glycerin or propylene glycol and combinations thereof. European Patent Number EP283165B1 discloses other suitable plasticizers, including glycerol derivatives such as propoxylated glycerol.

4. Optional Ingredients

The porous dissolvable solid substrate may further comprise other optional ingredients that are known for use or otherwise useful in personal care compositions, provided that such optional materials are compatible with the selected essential materials described herein, or do not otherwise unduly impair the performance of the personal care composition.

Such optional ingredients are most typically those materials approved for use in cosmetics and that are described in reference books such as the CTFA Cosmetic Ingredient Handbook, Second Edition, The Cosmetic, Toiletries, and Perfume Association, Inc. 1988, 1992. Examples of such optional ingredients are disclosed in U.S. Publication 2009/0232873A1, dated Sep. 17, 2009; U.S. Publication 2004/0092521A1, dated May 13, 2004; and US Publication 2003/0215522A1, dated Nov. 20, 2003.

Other optional ingredients include organic solvents, especially water miscible solvents and co-solvents useful as solubilizing agents for polymeric structurants and as drying accelerators. Examples of suitable organic solvents are disclosed in U.S. Ser. Publication 2009/0232873A1. Other optional ingredients include: latex or emulsion polymers, thickeners such as water soluble polymers, clays, silicas, ethylene glycol distearate, deposition aids, including coacervate forming components. Additional optional ingredients include antidandruff actives including but not limited to zinc pyrithione, selenium sulfide and those actives disclosed in US Publication 2003/0215522A1.

B. Surface Resident Coating Comprising a Starch Perfume Complex

In one embodiment, the porous dissolvable solid substrates provide a continuous and accessible high surface area "scaffold" (a 3-D network of "struts") for the surface resident coating comprising the starch perfume complex to be adsorbed or distributed across creating a high surface area thin coating. This location puts the coating in position to immediately contact water during use, releasing the perfumes from the encapsulate.

In one embodiment the surface resident coating comprises from about 10% to about 100% of one or more starch perfume complexes; in another embodiment from about 25% to about 100%, and in yet another embodiment from about 40% to about 100%. In one embodiment the ratio of the porous dissolvable solid substrate to the surface resident coating comprising the starch perfume complex is from about 110:1 to about 0.5:1, in another embodiment from about 20:1 to about 1:1, in another embodiment from about 10:1 to about 1.5:1, and in yet another embodiment from about 7:1 to about 3:1.

Starch Perfume Complexes

The ratio of the starch to perfume in the starch perfume complex is in one embodiment from about 0.5:1 to about 19:1, in another embodiment from about 0.7:1 to about 6:1, and in yet another embodiment from about 1:1 to about 3:1.

Perfumes suitable for use herein include any perfumes suitable for use in a personal care product including the use of primary and secondary perfumes as defined herein below.

Primary Perfume

Personal care compositions of the present invention comprise a primary perfume which provides the article with the desired perfume or unscented/neutral aroma prior to use (i.e., prior to contacting the article with water). The scented primary perfume may include any perfume or perfume chemical suitable for topical application to the skin and suitable for use in personal care compositions.

The concentration of the primary perfume in the personal care compositions should be effective to provide the desired aroma including, but not limited to, unscented. Generally, the concentration of the scented primary perfume is from about 0.0% to about 30.0%, in one embodiment from about 1% to about 20%, in yet another embodiment from about 2% to about 10%, and in yet another embodiment from about 3% to about 8%, by weight of the solid article. The primary perfume may be included in the personal care compositions of the present invention as a free perfume.

Secondary Perfume

In order to provide a secondary perfume shift (e.g., a change from one perfume to another), the secondary perfume of the present invention should be substantially different and distinct from the composition of the primary perfume in order to overcome the effect of perfume habituation and to make the second perfume noticeable over the primary perfume. Alternatively, where the same perfume is desired throughout the article's usage, the secondary perfume should be substantially the same and indistinct from the composition of the primary perfume in order to provide a single, continuous, long-lasting perfume experience.

Generally, personal care compositions of the present invention may comprise a secondary perfume from about 0.1%, to about 30.0%, in particular embodiments from about 1% to about 20%, in other embodiments from about 2% to about 10%, and in still other embodiments from about 3% to about 8%, by weight of the solid article.

Any perfume or perfume chemical suitable for topical application to the skin and suitable for use in personal care compositions may be used as the secondary perfume, however, it will not be included within the composition as a free perfume. The secondary perfume will be included in a surfactant-free and water-releasable matrix. The secondary perfume may be selected from the group consisting of perfumes, highly volatile perfume materials having a boiling point of less than about 250° C., and mixtures thereof. Such perfumes will be included within a water-releasable matrix formed from an encapsulating material, as described herein.

In one embodiment, the secondary perfume is selected from high impact accord perfume ingredients having a ClogP of greater than about 2 and odor detection thresholds of less than or equal to 50 parts per billion (ppb). The one or more primary and/or secondary perfumes may be complexed within water-releasable matrices comprised of starch or modified starch in particulate form. The ratio of the starch to perfume in the complex is in one embodiment from about 0.5:1 to about 19:1, in another embodiment from about 0.7:1 to about 6:1, and in yet another embodiment from about 1:1 to about 3:1.

Starch

The starch perfume complexes of the present invention can be derived from wide variety of starch-based materials including starches derived from cereals, tubers, roots, legumes and fruits. Native starch sources can include corn, pea, potato, banana, barley, wheat, rice, sago, amaranth, tapioca, arrowroot, canna, sorghum, oat, cassaya, amioca, and waxy or high amylase varieties thereof.

The starch-based materials can include native starches that are modified using any modification known in the art, including physically modified starches examples of which include sheared starches or thermally-inhibited starches; chemically modified starches including those which have been crosslinked, acetylated, and organically esterified, hydroxyethylated, and hydroxypropylated, phosphorylated, and inorganically esterified, cationic, anionic, nonionic, amphoteric and zwitterionic, and succinate and substituted succinate derivatives thereof; conversion products derived from any of the starches, including fluidity or thin-boiling starches prepared by oxidation, enzyme conversion, acid hydrolysis, heat or acid dextrinization, thermal and or sheared products may also be useful herein; and pregelatinized starches which are known in the art.

Starch based materials that are suitable for use herein include those wherein the starch is gelatinised and comprising hydrophobic groups including an alkyl, or an alkenyl group which contains at least five carbon atoms or an aralkyl or aralkenyl group which contains at least six carbon atoms. In one embodiment starches for use in the present invention are starch esters. These will typically have a degree of substitution in the range of from 0.01% to 10%. The hydrocarbon part of the modifying ester should be a C5 to a C16 carbon chain. In one embodiment the ester is octenyl succinate. In another embodiment octenyl succinate (OSAN) substituted waxy corn starches of various types such as 1) waxy starch, acid thinned and OSAN substituted, (2) blend of corn syrup solids: waxy starch, OSAN substituted and dextrinized, 3) waxy starch: OSAN substituted and dextrinised, 4) blend of corn syrup solids or maltodextrins with waxy starch: acid thinned OSAN substituted then cooked and spray dried, 5) waxy starch: acid thinned OSAN substituted then cooked and spray dried; and 6) the high and low viscosities of the above modifications (based on the level of acid treatment) can also be used in the present invention. Mixtures of these, particularly mixtures of the high and low viscosity modified starches are also suitable.

In one embodiment the modified starches comprise a starch derivative containing a hydrophobic group or both a hydrophobic and a hydrophilic group which has been degraded by at least one enzyme capable of cleaving the 1,4 linkages of the starch molecule from the non-reducing ends to produce short chained saccharides to provide high oxidation resistance while maintaining substantially high molecular weight portions of the starch base. Such starches are described in EP-A-922 449.

The starch or modified starch perfume complex may also include a plasticizer for the starch or modified starch. Suitable examples include monosaccharides, disaccharides, oligosaccharides and maltodextrins, such as glucose, sucrose, sorbitol, gum arabic, guar gums and maltodextrin.

Starch based materials suitable for use herein include acid modified starches, enzymatic hydrolyzed starches, octenyl succinic acid anhydride modified starches (OSAN starches), dextrinized OSAN starches, dextrins, maltodextrins, pregelatinized waxy maize starches, and mixtures thereof. Suitable examples of such starch based materials include, but are not limited to, CAPSUL™, CAPSUL TA™, HI-CAP 100™, CAPSUL E™, NARLEX™ (ST and ST2), AND N-LOK™, manufactured by Akzo Nobel (Bridgewater, N.J.); the EmCap™ series including 12633, 12634, 12635, 12639, 12635, and 12671, manufactured by Cargill Inc. (Cedar Rapids, Iowa); and STA-DEX® 90 and MIRA-CAP® Starch, manufactured by Tate & Lyle (Decatur, Ill.). Other examples of modified starches suitable for the present invention are disclosed for example in WO 99/55819, WO 01/40430, EP-A-858828, EP-A-1160311 and U.S. Pat. No. 5,955,419.

The particulate starch perfume complexes according to the present invention are anhydrous. However, water remnants are likely to be present even immediately after manufacture as a result of processing limitations. It may typically occur that water will re-enter the particulate complexes subsequently, for example during storage. The aqueous phase may not only comprise water, but may also comprise additional water-soluble components, such as alcohols; humectants, including polyhydric alcohols (e.g. glycerine and propylene glycol); active agents such as d-panthenol, vitamin $B_3$ and its derivatives (such as niacinamide) and botanical extracts; thickeners and preservatives. The aqueous phase does not represent more than 20% by weight of the encapsulate and may comprise from about 0.001% but no more than about 20%, no more than about 10%, no more than about 5%, or no more than about 2%, by weight of the particulate complex.

The particulate starch perfume complexes according to the invention may have a particle size from about 1 μm to about 200 μm, in another embodiment from about 2 μm to about 100 μm, and in yet another embodiment from about 3 μm to about 50 μm.

The surface resident coating is applied to the porous dissolvable solid substrate. In one embodiment, the surface resident coating is in the form of a fine powder. As seen in FIG. 1, in certain embodiments of the present invention, the personal care article 10 contains a surface resident coating 12 that is located on at least a portion of the surface of the porous dissolvable solid substrate 14. It will be appreciated that the surface resident coating 12 may not always be adjacent to the porous dissolvable solid substrate 14. In certain embodiments, the surface resident coating 12 may permeate the porous dissolvable solid substrate 14 in whole or in part.

Figure 3A:
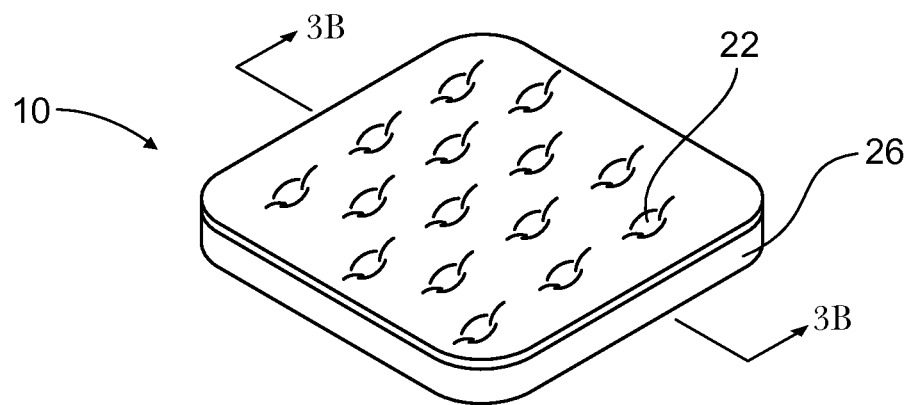
FIGS. 3A, and 3B are a schematic view of a dimpled porous dissolvable solid substrate with a surface resident starch perfume complex inside the dimples.
Figure 3B:
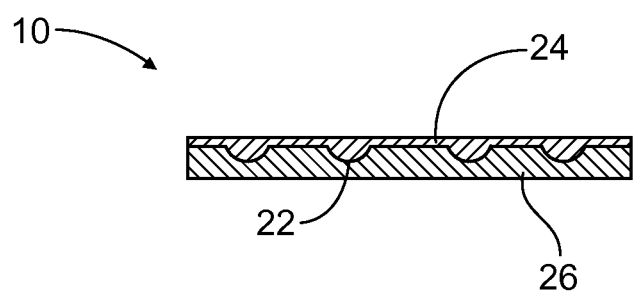

Alternatively, the surface resident coating can be included (e.g., sandwiched or encased) within the personal care article or parts thereof. Such a surface resident coating can be sprayed, dusted, sprinkled, coated, surface-printed (e.g., in the shape of a desired adornment, decoration, or pattern), poured on, injected into the interior, dipped, or by any other suitable means, such as by use of a depositor, sifter, or powder bed. In the embodiments depicted by FIGS. 3A, 3B, and 4, the personal care article 10 contains a surface resident coating that can be situated below the surface of the porous dissolvable solid substrate. As seen in FIG. 3B which is a cross sectional view of the personal care article 10, the surface resident coating 24 is located within the dimples 22 of the porous dissolvable solid substrate 26.

Figure 2:
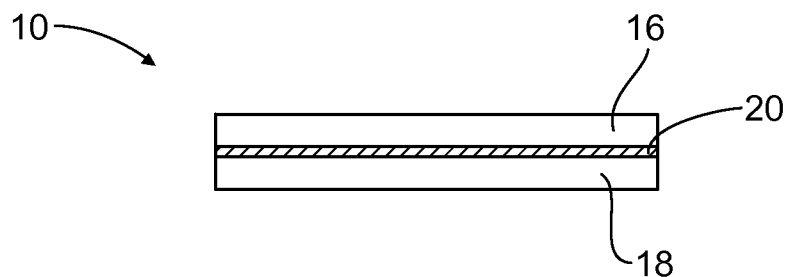
FIG. 2 is a schematic view of two porous dissolvable solid substrates with a surface resident starch perfume complex layer in between the two substrates.

Referring now to FIG. 2, in certain embodiments the powder is sandwiched between two porous dissolvable solid substrate which are then joined together (e.g., via sealing the adjoining surfaces or edges with a thin layer of water and/or plasticizer so as to not substantially dissolve the porous dissolvable solid substrate and applied pressure to induce adhesion). In this embodiment, the personal care article 10 comprises two porous dissolvable solid substrates 16, 18 in between which a surface resident coating 20 is located.

Figure 4:
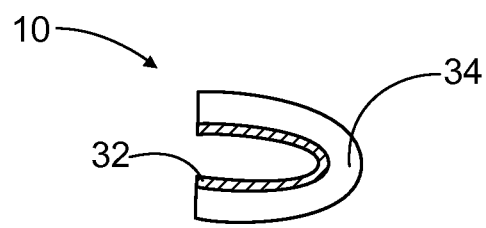
FIG. 4 is a schematic view of a porous dissolvable solid substrate that is folded over to enclose a surface resident starch perfume complex.

Alternatively, in certain embodiments, the powder may be on one personal care article which is folded over to form a pouch, encasing the powder. As depicted in FIG. 4, the personal care article 10 comprises a surface resident coating 32 that is enclosed within a folded porous dissolvable solid substrate 34.

The surface resident starch perfume complex coatings of the present invention may also impart other desirable attributes to the personal care article including, but not limited to, improved visual appearance. Moreover, the surface resident starch perfume complex coatings of the present invention may provide additional benefits such as imparting antistick properties to minimize sticking of the article to the product packaging or to other articles in the case to where they are delivered as a stack of articles.

III. PRODUCT FORM OF THE PERSONAL CARE ARTICLE

The personal care article can be produced in any of a variety of product forms, including porous dissolvable solid substrates along with the surface resident coating comprising the starch perfume complex used alone or in combination with other personal care components. Regardless of the product form, the product form embodiments contemplated herein include the selected and defined personal care article that comprises a combination of a porous dissolvable solid substrate and a surface resident coating comprising a starch perfume complex.

In one embodiment, the personal care article is in the form of one or more flat sheets or pads of an adequate size to be able to be handled easily by the user. It may have a square, rectangle or disc shape or any other suitable shape. The pads can also be in the form of a continuous strip including delivered on a tape-like roll dispenser with individual portions dispensed via perforations and or a cutting mechanism. Alternatively, the personal care articles are in the form of one or more cylindrical objects, spherical objects, tubular objects or any other shaped object.

The personal care article may comprise one or more textured, dimpled or otherwise topographically patterned surfaces including letters, logos or figures. The textured substrate can result from the shape of the substrate, in that the outermost surface of the substrate contains portions that are raised with respect to other areas of the surface. The raised portions can result from the formed shape of the personal care article, for example the personal care article can be formed originally in a dimpled or waffle pattern. The raised portions can also be the result of creping processes, imprinted coatings, embossing patterns, laminating to other layers having raised portions, or the result of the physical form of the porous dissolvable solid substrate itself. The texturing can also be the result of laminating one porous dissolvable solid substrate to a second porous dissolvable solid substrate that is textured. In a particular embodiment, the personal care article can be perforated with holes or channels penetrating into or through the porous solid.

IV. METHOD OF MANUFACTURE

The personal care article can be prepared by the process comprising: (1) Preparing a processing mixture comprising surfactant(s), dissolved polymer structurant, and plasticizer; (2) Aerating the processing mixture by introducing a gas into the processing mixture to form an aerated wet mixture; (3) Forming the aerated wet mixture into one or more desired shapes; (4) Drying the aerated wet mixture to form a porous dissolvable solid substrate; and (5) Applying the surface resident coating comprising a starch perfume complex in powdered form to the porous dissolvable solid substrate.

A. Preparation of Processing Mixture

The processing mixture is generally prepared by dissolving the polymer structurant in the presence of water, plasticizer, surfactant and other optional ingredients by heating followed by cooling. This can be accomplished by any suitable heated batch agitation system or via any suitable continuous system involving either single screw or twin screw extrusion or heat exchangers together with either high shear or static mixing. Any process can be envisioned such that the polymer is ultimately dissolved in the presence of water, the surfactant(s), the plasticizer, and other optional ingredients including stepwise processing via pre-mix portions of any combination of ingredients.

The processing mixtures of the present invention comprise: from about 15% to about 60% solids, in one embodiment from about 20% to about 55% solids, in another embodiment from about 25% to about 50% solids, and in yet another embodiment from about 30% to about 45% solids by weight of the processing mixture before drying; and have a viscosity of from about 2,500 cps to about 150,000 cps, in one embodiment from about 5,000 cps to about 100,000 cps, in another embodiment from about 7,500 cps to about 75,000 cps, and in still another embodiment from about 10,000 cps to about 60,000 cps.

The % solids content is the summation of the weight percentages by weight of the total processing mixture of all of the solid, semi-solid and liquid components excluding water and any obviously volatile materials such as low boiling alcohols. The processing mixture viscosity values are measured using a TA Instruments AR500 Rheometer with 4.0 cm diameter parallel plate and 1,200 micron gap at a shear rate of 1.0 reciprocal seconds for a period of 30 seconds at 23° C.

B. Aeration of Processing Mixture

The aeration of the processing mixture is accomplished by introducing a gas into the mixture. In one embodiment this is done by mechanical mixing energy. In another embodiment this may be achieved via chemical means. The aeration may be accomplished by any suitable mechanical processing means, including but not limited to: (i) Batch tank aeration via mechanical mixing including planetary mixers or other suitable mixing vessels, (ii) semi-continuous or continuous aerators utilized in the food industry (pressurized and non-pressurized), or (iii) spray-drying the processing mixture in order to form aerated beads or particles that can be compressed such as in a mould with heat in order to form the porous solid.

In a particular embodiment, it has been discovered that the personal care article can be prepared within continuous pressurized aerators that are conventionally utilized within the foods industry in the production of marshmallows. Suitable continuous pressurized aerators include the Morton whisk (Morton Machine Co., Motherwell, Scotland), the Oakes continuous automatic mixer (E.T. Oakes Corporation, Hauppauge, N.Y.), the Fedco Continuous Mixer (The Peerless Group, Sidney, Ohio), and the Preswhip (Hosokawa Micron Group, Osaka, Japan).

Aeration can also be accomplished with chemical foaming agents by in-situ gas formation (via chemical reaction of one or more ingredients, including formation of carbon dioxide ($CO_2$ (g)) by an effervescent system. An additional possibility is aeration via volatile blowing agents such as low boiling hydrocarbons or alcohols including, but not limited to, isopentane, pentane, isobutene, ethanol etc.

In one embodiment, the pre-mixture is pre-heated immediately prior to the aeration process at above ambient temperature but below any temperatures that would cause undesirable degradation of any of the components. In one embodiment, the pre-mixture is kept at above about 40° C. and below about 99° C., in another embodiment above about 50° C. and below about 95° C., in another embodiment above about 60° C. and below about 90° C. In one embodiment, when the viscosity at ambient temperature of the pre-mix is from about 20,000 cps to about 150,000 cps, the optional continuous heating should be utilized before the aeration step. In another embodiment, additional heat is applied during the aeration process to try and maintain an elevated temperature during the aeration. This can be accomplished via conductive heating from one or more surfaces, injection of steam, a surrounding hot water bath, or other processing means.

In one embodiment the wet density range of the aerated pre-mixture ranges from about 0.12 $g/cm^3$ to about 0.50 $g/cm^3$, in another embodiment from about 0.15 $g/cm^3$ to about 0.45 $g/cm^3$, in another embodiment from about 0.20 $g/cm^3$ to about 0.40 $g/cm^3$, and in yet another embodiment from about 0.25 $g/cm^3$ to about 0.35 $g/cm^3$.

C. Forming the Aerated Wet Processing Mixture

The forming of the aerated wet processing mixture may be accomplished by any suitable means to form the mixture in a desired shape or shapes including, but not limited to (i) depositing the aerated mixture to moulds of the desired shape and size comprising a non-interacting and non-stick surface including aluminium, Teflon, metal, HDPE, polycarbonate, neoprene, rubber, LDPE, glass and the like; (ii) depositing the aerated mixture into cavities imprinted in dry granular starch contained in a shallow tray, otherwise known as starch moulding forming technique; and (iii) depositing the aerated mixture onto a continuous belt or screen comprising any non-interacting or non-stick material Teflon, metal, HDPE, polycarbonate, neoprene, rubber, LDPE, glass and the like which may be later stamped, cut, embossed or stored on a roll.

D. Drying the Aerated Wet Processing Mixture into a Porous Dissolvable Solid Substrate The drying of the formed aerated wet processing mixture may be accomplished by any suitable means including, but not limited to (i) drying room(s) including rooms with controlled temperature and pressure or atmospheric conditions; (ii) ovens including non-convection or convection ovens with controlled temperature and optionally humidity; (iii) Truck/Tray driers, (iv) multi-stage inline driers; (v) impingement ovens; (vi) rotary ovens/driers; (vii) inline roasters; (viii) rapid high heat transfer ovens and driers; (ix) dual plenum roasters, and (x) conveyor driers, and combinations thereof. Any suitable drying means that does not comprise freeze-drying can be used.

The drying temperature may range from about 40° C. to about 200° C. In a one embodiment, the drying environment is heated to a temperature between 100° C. and 150° C. In one embodiment, the drying temperature is between 105° C. and 145° C. In another embodiment, the drying temperature is between 110° C. and 140° C. In a further embodiment, the drying temperature is between 115° C. and 135° C.

Other suitable drying environments include "volumetric heating" techniques using high frequency electromagnetic fields such as Microwave Drying and Radio Frequency (RF) Drying. With these techniques, the energy is transferred electromagnetically through the aerated wet pre-mixture rather than by conduction or convection.

Optional ingredients may be imparted during any of the above described four processing steps or even after the drying process.

E. Preparing the Surface Resident Coating Comprising the Starch Perfume Complex

The preparation of the surface resident coating comprising the starch perfume complex may include any suitable mechanical or otherwise physical means to produce a particulate composition comprising the starch perfume complex as described herein. In one embodiment, the starch perfume complexes of the present invention are prepared by spray drying wherein the perfume is dispersed or emulsified within an aqueous composition comprising the dissolved starch based material under high shear (with optional emulsifying agents) and spray dried into a fine powder. The optional emulsifying agents can include gum arabic, specially modified starches, or other tensides as taught in the spray drying art (See Flavor Encapsulation, edited by Sara J. Risch and Gary A. Reineccius, pages 9, 45-54 (1988), which is incorporated herein by reference).

Other known methods of manufacturing the starch perfume complexes of the present invention may include but are not limited to, fluid bed agglomeration, extrusion, cooling/crystallisation methods and the use of phase transfer catalysts to promote interfacial polymerisation.

Alternatively, the perfume oil can be adsorbed or absorbed into or combined with a starch based powder that has been previously produced via a variety of mechanical mixing means (spray drying, paddle mixers, grinding, milling etc.). In one embodiment, the starch based material in either pellet or granular or other solid-based form (and comprising any minor impurities as supplied by the supplier including residual solvents and plasticizers) may be ground or milled into a fine powder in the presence of the perfume via a variety of mechanical means, for instance in a grinder or hammer mill.

In one embodiment the surface resident coatings of the present invention may have a particle size from about 1 µm to about 200 µm, in another embodiment from about 2 µm to about 100 µm, and in yet another embodiment from about 3 µm to about 50 µm.

In some embodiments, inert fillers can be included within the particulate complex forming process or particulate complex after forming, for instance aluminum starch octenylsuccinate under the trade name DRY-FLO® PC and available from Akzo Nobel, at a level sufficient to improve the flow properties of the powder and to mitigate inter-particle sticking or agglomeration during powder production or handling. Other optional excipients or cosmetic actives, as described herein, can be incorporated into the powder during the particulate complex forming process. The resulting powder may also be blended with other powders, either of inert materials or other powder-active complexes as described herein.

F. Combining Surface Resident Coating Comprising the Starch Perfume Complexes with the Porous Dissolvable Solid Substrate Any suitable application method can be used to apply the surface resident coating comprising the starch perfume complex to the personal care article such that it forms a part of the personal care article. For instance, the porous dissolvable solid substrate can have a tacky surface by drying the porous dissolvable solid substrate's surface to a specific water content before application of powder to facilitate the adherence of the surface resident coating comprising the starch perfume complex to the porous solid. In one embodiment, the porous dissolvable solid substrate is dried to a moisture content of from about 0.1% to about 25%, in one embodiment from about 3% to about 25%, in another embodiment from about 5% to about 20% and in yet another embodiment from about 7% to about 15%. Alternatively, a previously dried dissolvable porous solid substrate's surface can be made to reversibly absorb a desired level of atmospheric moisture prior to application of the powder within a controlled humidity environment for a specific period of time until equilibrium is achieved. In one embodiment, the humidity environment is controlled from about 20% to about 85% relative humidity; in another embodiment, from about 30% to about 75% relative humidity; and in yet another embodiment, from about 40% to about 60% relative humidity.

In another embodiment, the porous dissolvable solid substrate is placed in a bag, tray, belt, or drum containing or otherwise exposed to the powder and agitated, rolled, brushed, vibrated or shaken to apply and distribute the powder, either in a batch or continuous production manner. Other powder application methods may include powder sifters, electrostatic coating, tribo charging, fluidized beds, powder coating guns, corona guns, tumblers, electrostatic fluidized beds, electrostatic magnetic brushes, and/or powder spray booths. The surface resident coating comprising the starch perfume complex can be applied over portions or entire regions of the porous dissolvable solid substrate's exterior surface, and can be applied in a manner to adorn, decorate, form a logo, design, etc.

V. TEST METHODS

A. Dissolution Rate

The personal care article of present invention has a Dissolution Rate that allows the personal care article to rapidly disintegrate during use application with water. The Dissolution Rate of the personal care article is determined in accordance with the methodology described below.

Hand Dissolution Method: 0.5 to 1.5 g (approximately 10 to 20 square centimeters if in a 3 to 10 mm thick sheet/pad form) of the personal care article (as described in the examples herein) is placed in the palm of the hand while wearing nitrile gloves. 7.5 $cm^3$ of warm tap water (from about 30° C. to about 35° C.) is quickly applied to the personal care composition via syringe. Using a circular motion, palms of hands are rubbed together 2 strokes at a time until dissolution occurs (up to 30 strokes). The hand dissolution value is reported as the number of strokes it takes for complete dissolution or as 30 strokes as the maximum. For the latter scenario, the weight of the undissolved material is also reported.

The personal care articles of the present invention have a hand dissolution value of from about 1 to about 30 strokes, in one embodiment from about 2 to about 25 strokes, in another embodiment from about 3 to about 20 strokes, and in still another embodiment from about 4 to about 15 strokes.

B. Thickness

The thickness of the personal care article and/or the porous dissolvable solid substrate is obtained using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1 inch diameter platen weighing about 32 grams, which measures thickness at an application pressure of about 40.7 phi (6.32 gm/cm$^2$).

The thickness of the personal care article and/or the porous dissolvable solid substrate is measured by raising the platen, placing a section of the sample on the stand beneath the platen, carefully lowering the platen to contact the sample, releasing the platen, and measuring the thickness of the sample in millimeters on the digital readout. The sample should be fully extended to all edges of the platen to make sure thickness is measured at the lowest possible surface pressure, except for the case of more rigid samples which are not flat. For more rigid samples which are not completely flat, a flat edge of the sample is measured using only one portion of the platen impinging on the flat portion of the sample. In the case of cylindrical, spherical, or other objects with more of a third dimension versus a pad or strip, the thickness is taken as the maximum distance of the shortest dimension, i.e., the diameter of a sphere or cylinder for instance, and the thickness ranges are the same as described above.

C. Basis Weight

The Basis Weight of the personal care article and/or the porous dissolvable solid substrate is calculated as the weight of the personal care article and/or the porous dissolvable solid substrate per area of the selected personal care article and/or the porous dissolvable solid substrate (grams/m$^2$). The area is calculated as the projected area onto a flat surface perpendicular to the outer edges of the personal care article and/or the porous dissolvable solid substrate. For a flat object, the area is thus computed based on the area enclosed within the outer perimeter of the sample. For a spherical object, the area is thus computed based on the average diameter as 3.14× (diameter/2)$^2$. For a cylindrical object, the area is thus computed based on the average diameter and average length as diameter×length. For an irregularly shaped three dimensional object, the area is computed based on the side with the largest outer dimensions projected onto a flat surface oriented perpendicularly to this side.

D. Solid Density

The porous dissolvable solid substrate of the personal care compositions described herein can be characterized in terms of a solid density determination.

The solid density of the porous dissolvable solid substrate can be determined by dividing the weight of the solid by the known volume of the solid. The latter can be determined by a number of techniques including producing the solid within a mold of known x-y dimensions and measuring the resulting thickness to account for any shrinkage or expansion during the drying process. The solid can also be cut to known x-y dimensions, i.e., by using a circular or square cutting die of known diameter or dimensions and then by measuring the thickness. Alternatively, in the instances where there are not any significant thickness variations, the density can be calculated by the equation: Calculated Density=Basis Weight of porous solid/(Average porous Solid Thickness×1,000).

E. Cell Inter-Connectivity

The personal care article and/or the porous dissolvable solid substrate of the present invention have a high degree of cell inter-connectivity, i.e., are predominantly open-celled solid foams as opposed to being predominantly closed-cell solid foams. The cell inter-connectivity can be assessed by light microscopy, scanning electron microscopy, micro computed tomography imaging parameters (Star Volume and SMI Index), gas pyncnometry parameters (% Open Cells), or other suitable methodology.

A qualitative method of determining cell inter-connectivity is via light microscopy. This is performed by cutting a 2-3 mm wide sliver of the personal care article and/or the porous dissolvable solid substrate in the z-direction using scissors or a sharp blade, measured across the normal x-y largest surface, and turning the resulting sliver by 90 degrees to reveal the internal cellular structure of the freshly cut cross-sectional area. This cross-sectional area can be assessed by close visual inspection or, more accurately, by employing magnification under a stereo microscope such as the SZX12 Stereo microscope available from Olympus Olympus America Inc., Center Valley, Pa. The open-celled personal care article and/or the porous dissolvable solid substrate of the present invention can easily be identified by examining the inner portion of the cross-sectional area which will comprise a predominantly three dimensional network of struts with open void spaces surrounding the struts that are inter-connected to one another including in the third dimension through the depth of the cross-section. In contrast, the inner cross-section of a closed-cell foam will appear as discrete bubbles that are cut across and then only being inter-connected at the cross-sectional surface in two dimensions by virtue of the cutting process employed to generate the exposed cross-sectional area.

Another means to determine the cell interconnectivity is via the Star Volume and the Structure Model Index. Disk-like samples, approximately 4 cm in diameter and 3 to 7 mm high, are scanned using a micro computed tomography system (μCT80, SN 06071200, Scanco Medical AG). Each sample is imaged while sitting flat on the bottom of a cylindrical tube. Image acquisition parameters are 45 kVp, 177 μA, 51.2 mm field of view, 800 ms integration time, 1000 projections. The number of slices is adjusted to cover the height of the sample. The reconstructed data set consisted of a stack of images, each 2048×2048 pixels, with an isotropic resolution of 25 μm. For data analysis, a volume of interest is selected to be fully within the sample, avoiding the surface region. A typical volume of interest is 1028×772×98 voxels.

Structure Model Index (SMI) is measured using Scanco Medical's Bone Trabecular Morphometry evaluation with a threshold of 17. With this index the structural appearance of trabecular bone is quantified (see T. Hildebrand, P. Rüegsegger. Quantification of bone microarchitecture with the structure model index. *Comp Meth Biomech Biomed Eng* 1997; 1:15-23). The triangulated surface is dilated in normal direction by an infinitesimal amount, and the new bone surface and volume is calculated. By this, the derivative of the bone surface (dBS/dr) can be determined. The SMI is then represented by the equation:

$$SMI = 6 \cdot \frac{BV \cdot \frac{dBS}{dr}}{BS^2}$$

SMI relates to the convexity of the structure to a model type. Ideal (flat) plates have an SMI of 0 (no surface change with dilation of the plates), whereas ideal cylindrical rods have an SMI of 3 (linear increase in surface with dilation of rods). Round spheres have an SMI of 4. Concave structure gives negative dBS/dr, resulting in negative SMI values. Artificial boundaries at the edge of the volume of interest are not included in the calculation and thus suppressed.

In addition to the Scanco Medical Analysis, StarVolume measurements are made. Star Volume is a measure of the "openness" of the void space in a two phase structure. By choosing a random uniformly distributed set of points in the phase of interest (in our case this is the background), we can extend lines in random directions from each of these points. The lines are extended until they touch the foreground phase. The length of each of these lines is then recorded. The random points have a sampling of 10 in each direction (x/y/z) and at each point 10 random angles are chosen. If the line extends to the border of the ROI of interest that line is discarded (we only want to accept lines that actually intersect with the foreground phase). The final equation is based upon the research published in *Star volume in bone research. A histomorphometric analysis of trabecular bone structure using vertical sections*; Vesterby, A.; Anat Rec.; 1993 February; 235(2):325-334:

$$StarVolume = \frac{4}{3}\pi \cdot \frac{\sum dist^3}{N}$$

where "dist" is the individual distances and N is the number of lines examined.

The Percent Open Cell Content is measured via gas pycnometry. Gas pycnometry is a common analytical technique that uses a gas displacement method to measure volume accurately. Inert gases, such as helium or nitrogen, are used as the displacement medium. The sample is sealed in the instrument compartment of known volume, the appropriate inert gas is admitted, and then expanded into another precision internal volume. The pressure before and after expansion is measured and used to compute the sample volume. Dividing this volume into the sample weight gives the gas displacement density.

ASTM Standard Test Method D2856 provides a procedure for determining the percentage of open cells using an older model of an air comparison pycnometer. This device is no longer manufactured. However, you can determine the percentage of open cells conveniently and with precision by performing a test which uses Micromeritics' AccuPyc Pycnometer. The ASTM procedure D2856 describes 5 methods (A, B, C, D, and E) for determining the percent of open cells of foam materials.

For these experiments, the samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the true volume as measured by the Accupyc. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde Orr and Paul Webb.

F. Cell Wall Thickness

The Cell Wall Thickness of the personal care article and/or the porous dissolvable solid substrate is computed from the scanned images via a micro computed tomography system (μCT80, SN 06071200, Scanco Medical AG) as described herein. The Cell Wall Thickness is determined according to the method defined for the measurement of Trabecular Thickness using Scanco Medical's Bone Trabecular Morphometry evaluation. The definition of Trabecular Thickness as taken from the Scanco User's manual: Trabecular Thickness uses a Euclidean distance transformation (EDM), which calculates the Euclidean distance from any point in the foreground to the nearest background point. The Trabecular Thickness measure represents twice the centerline values associated with the local maxima of the EDM, which represents the distance to the center of the object (twice this distance will yield the thickness).

G. Specific Surface Area

The Specific Surface Area of the personal care article and/or the porous dissolvable solid substrate is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the degassed sample+sample tube weight. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved.

Sample Preparation (Degassing): A sample not adequately cleaned of adsorbed contaminants will outgas during an analysis and some portion of the surface will be inaccessible to measurement. The purpose of degassing is to remove these adsorbed molecules from the surface of the sample prior to analysis. Adsorptive molecules must reach all parts of the surface for the true surface area to be revealed. Samples are prepared by heating the sample while simultaneously evacuating the sample tube.

For these experiments, the samples are outgassed under evacuation at room temperature overnight. Samples may then analyzed using an ASAP 2420 with krypton gas adsorption. Krypton gas is preferred over nitrogen gas as it has a saturation pressure approximately 1/300 that of nitrogen at liquid nitrogen temperature (krypton: 2.5 torr; nitrogen: 760 torr). Therefore, compared to nitrogen, there is in the free space above the sample about 1/300 the number of krypton molecules present at the same relative pressure. Since about the same number of krypton and nitrogen molecules are required to form a monolayer, this number represents a far greater proportion of the quantity dosed than in the case of nitrogen. These measurements can be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde On and Paul Webb.

H. Evaluation of Surface Resident Coating

The presence of a surface resident coating comprising a starch-perfume complex of the present invention can be determined by a number of techniques. For detection of a particulate or powder coating, the surface of application as well as the cross-sections perpendicular to the larger surfaces of the porous dissolvable solid substrate can be examined by microscopic techniques. These microscopic techniques may include light microscopy and scanning electron microscopy (SEM). The light microscopy may include but are not necessarily limited to bright field, dark field, or confocal microscopy techniques. Other techniques for mapping unique elements such as silicon or distinctive functional groups such as quaternary ammonium groups on the cross-sectional surface include: time of flight secondary ion mass spectroscopy (ToF-SIMS), or infrared microscopy.

Potential methods for looking at the distribution of particles from the surface to the interior of the porous dissolvable solid substrate without sectioning the samples include: micro-Computed Tomography (micro-CT), Magnetic Resonance Imaging (MRI), Acoustic Imaging, Confocal Fluorescence Microscopy, Confocal Raman Spectroscopy, and Confocal Infrared Reflectance Spectroscopy.

The determination of surface-resident coating particles on cross-sectioned porous dissolvable solid substrate can be performed by comparing the distribution of the particles across the cut cross-section of the porous solid. Specifically, the surface resident coating particles should be present at the original solid/air interfaces, but not within the exposed cross sectioned interior of the solid cell walls as can be ascertained by analyzing the exposed freshly cut cross-sectional interiors of the solid. It should be noted that some contamination of the freshly cut cross-sectional solid cell wall interiors may occur as a consequence of the cutting process of the porous solid. However, the preponderance (in one embodiment, from about 50% to about 100%) of the surface resident coating particle distribution will occur at the original solid/air interfaces and not within the exposed cut cross-sectional interiors of the cell walls.

It should also be noted that the surface resident coating particles of the present invention generally do not spread uniformly across all exposed solid/air interfaces. Rather, it has been found that the surface resident coatings of the present invention typically spread, from the point of coating application, into cavities down to about 0.5 to about 3.0 mm according to gravity. Accordingly, the determination of surface resident particles of cosmetic actives of the present invention (as described above), should be conducted across many different cross sections from top-to-bottom and from edge-to-edge of the porous solid. If present, the surface resident cosmetic active particle will generally be within the regional vicinity (to within about 0.5 to about 3.0 mm from the surface) of the surface to where the coating was first applied.

I. Expert Perfume Panel

An expert perfume sensory panel is conducted to quantify the perfume performance within a normal shampoo protocol regimen with three expert perfumers evaluating the odor character and odor intensity on a 1 to 100 scale (no odor to the most intense odor possible) as described below. A retail liquid shampoo product is included within each panel as a control leg (Herbal Essences Drama Clean Shampoo, Distributed by Procter & Gamble).

The expert perfume panel assessment is performed on 15 g/10" flat Oriental virgin hair switches. The hair switch is rinsed with 100° F. tap water at 1.5 to 2.0 gallons/min for 20 seconds with a shower nozzle. For testing the liquid control products, the liquids are first smelled in an open glass jar for the neat product odor. 5 cm³ of liquid product is then applied to the palm of a pre-wetted hand for the initial perfume bloom assessment in the hand. Next, the liquid is applied to the center of the switch with the palm and lathered for 40 seconds by repeatedly rubbing and squeezing the hair switch with both hands in a downward motion for the lather on switch odor assessment. The switch is then thoroughly rinsed for 45 seconds and assessed for wet hair odor. Additional assessments include the 4 hour damp hair odor, the 24 hour dry hair odor and the 24 hour re-wet odor.

When testing the dissolvable porous solids of the present invention, 1 substrate in the form of a pad (approximately 1.0 to 1.1 grams) is substituted for the 5 cm³ of liquid. For testing the dissolvable porous solids, the pad is first smelled in a freshly opened wrapper for the neat product odor. The pad is then applied to the palm of a pre-wetted hand and diluted with 7.5 ml of 100° F. tap water with rubbing of the palms (4 to 8 strokes) until the solid is fully dissolved for the initial perfume bloom assessment in the hand. Next, the resulting liquid mixture is applied to the center of the switch with the palm and lathered for 40 seconds by repeatedly rubbing and squeezing the hair switch with both hands in a downward motion for the lather on switch odor assessment. The switch is then thoroughly rinsed for 45 seconds and assessed for wet hair odor, 4 hour damp hair odor, 24 hour dry hair odor and 24 hour re-wet odor as described above.

IV. METHODS OF USE

The compositions of the present invention may be used for treating mammalian keratinous tissue such as hair and/or scalp, and provide rapid rinse-ability. The method for conditioning the hair may comprise the steps of: a) applying an effective amount of the personal care product to the hand, b) wetting the personal care product with water and rubbing to dissolve the solid, c) applying the dissolved material to either the hair or scalp such as to treat, and d) rinsing the diluted treatment from the hair or scalp using water. These steps can be repeated as many times as desired to achieve the desired treatment benefit.

V. EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Example 1

Preparation of Porous Dissolvable Solid Shampoo Substrate

The following surfactant/polymer liquid processing composition is prepared at the indicated weight percentages as described in Table 1 below.

TABLE 1

| | |
|---|---|
| Glycerin | 3.2 |
| Polyvinyl alcohol[1] | 8.1 |
| Sodium Lauroamphoacetate (26% activity)[2] | 31.8 |
| Ammonium Laureth-3 sulfate (25% activity) | 4.9 |
| Ammonium Undecyl sulfate (24% activity) | 19.9 |
| Ammonium Laureth-1 sulfate (70% activity) | 8.0 |
| Cationic cellulose[3] | 0.5 |
| Citric Acid | 1.6 |

TABLE 1-continued

| | |
|---|---|
| Distilled water | 22.0 |
| Total | 100.0 |
| pH | 5.8 |
| Viscosity (cp) | 35,400 |

[1]Sigma-Aldrich Catalog No. 363081, MW 85,000-124,000, 87-89% hydrolyzed
[2]McIntyre Group Ltd, University Park, IL, Mackam HPL-28ULS
[3]UCARE ™ Polymer LR-400, available from Amerchol Corporation (Plaquemine, Louisiana)

A target weight of 300 grams of the above composition is prepared with the use of a conventional overhead stirrer (IKA® RW20DZM Stirrer available from IKA® Works, Inc., Wilmington, Del.) and a hot plate (Corning Incorporated Life Sciences, Lowell, Mass.). Into an appropriately sized and cleaned vessel, the distilled water and glycerin are added with stirring at 100-150 rpm. The cationic polymer, when present, is then slowly added with constant stirring until homogenous. The polyvinyl alcohol is weighed into a suitable container and slowly added to the main mixture in small increments using a spatula while continuing to stir while avoiding the formation of visible lumps. The mixing speed is adjusted to minimize foam formation. The mixture is slowly heated to 80° C. after which surfactants are added. The mixture is then heated to 85° C. while continuing to stir and then allowed to cool to room temperature. Additional distilled water is added to compensate for water lost to evaporation (based on the original tare weight of the container). The final pH is between 5.2-6.6 and adjusted with citric acid or diluted sodium hydroxide if necessary. The resulting processing mixture viscosity is measured.

The porous dissolvable substrate (may be referred to in the examples herein as "substrate") was prepared from the above liquid processing mixture as described in Table 2 below.

TABLE 2

| | |
|---|---|
| Aeration Time (sec) | 62 |
| Wet Density (g/cm$^3$) | 0.26 |
| Oven Temperature (° C.) | 130 |
| Drying Time (min) | 38 |
| Average dry substrate weight (g) | 1.10 |
| Average dry substrate thickness (cm) | 0.62 |
| Average substrate shrinkage (%) | 4.6% |
| Average dry substrate density (g/cm$^3$) | 0.11 |
| Average basis weight (g/m$^2$) | 650 |

300 grams of the processing mixture (from Examples 1) is stored within a convection oven for greater than two hours at 70° C. to pre-heat the processing mixture. The mixture is then transferred into a pre-heated 5 quart stainless steel bowl (by placing into 70° C. oven for greater than 15 minutes) of a KITCHENAID® Mixer Model K5SS (available from Hobart Corporation, Troy, Ohio) fitted with a flat beater attachment and with a water bath attachment comprising tap water at 70-75° C. The mixture is vigorously aerated at a maximum speed setting of 10 until a wet density of approximately 0.26 grams/cm$^3$ is achieved (time recorded in table). The density is measured by weighing a filling a cup with a known volume and evenly scraping off the top of the cup with a spatula. The resulting aerated mixture is then spread with a spatula into square 160 mm×160 mm aluminum molds with a depth of 6.5 mm with the excess wet foam being removed with the straight edge of a large metal spatula that is held at a 45° angle and slowly dragged uniformly across the mold surface. The aluminum molds are then placed into a 130° C. convection oven for approximately 35 to 45 minutes. The molds are allowed to cool to room temperature with the substantially dry porous solids removed from the molds with the aid of a thin spatula and tweezers.

Each of the resulting 160 mm×160 mm square substrates is cut into nine 43 mm×43 mm squares (with rounded edges) using a cutting die and a Samco SB20 cutting machine (each square representing surface area of approximately 16.9 cm$^2$). The resulting smaller substrates are then equilibrated overnight (14 hours) in a constant environment room kept at 70° F. and 50% relative humidity within large zip-lock bags that are left open to the room atmosphere. Each substrate is then weighed and placed on an individual weight boat with the original mold side facing downward. The average substrate weights are recorded along with the substrate shrinkage (based on the original 6.5 mm mold depth). And the basis weight computed by dividing the average substrate weight by 0.00169 square meters. The resulting substrate thickness is measured with a digital caliper and recorded. The bags are sealed within the 50% relative humidity environment.

Example 2

Structural Characterization of Porous Dissolvable Solid Shampoo Substrate

The below Table 3 summarizes the structural measurements and qualitative physical integrity ratings taken on the dissolving porous shampoo solid of Example 1. SEM and micro-CT images were also taken and are referenced in the attached figures. The data was collected by the methods as described herein.

TABLE 3

Figure 5:
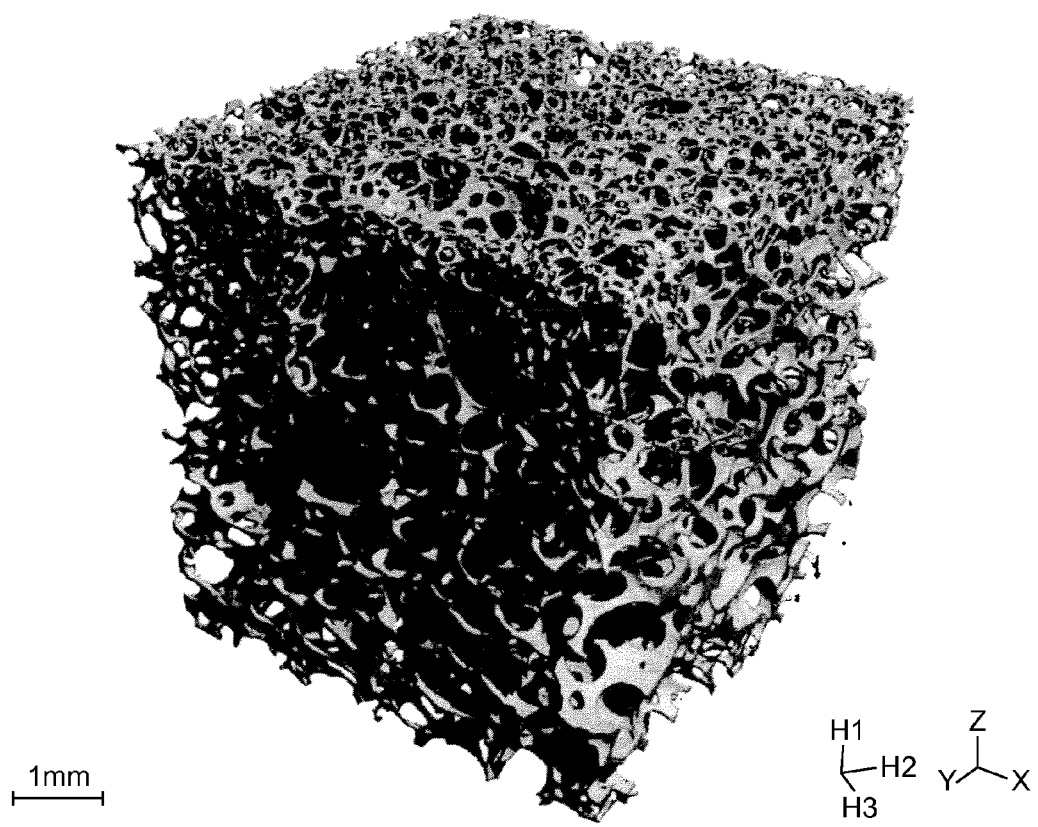
FIG. 5 is a Micro-CT 3-D Image of porous dissolvable solid substrate.
Figure 6:
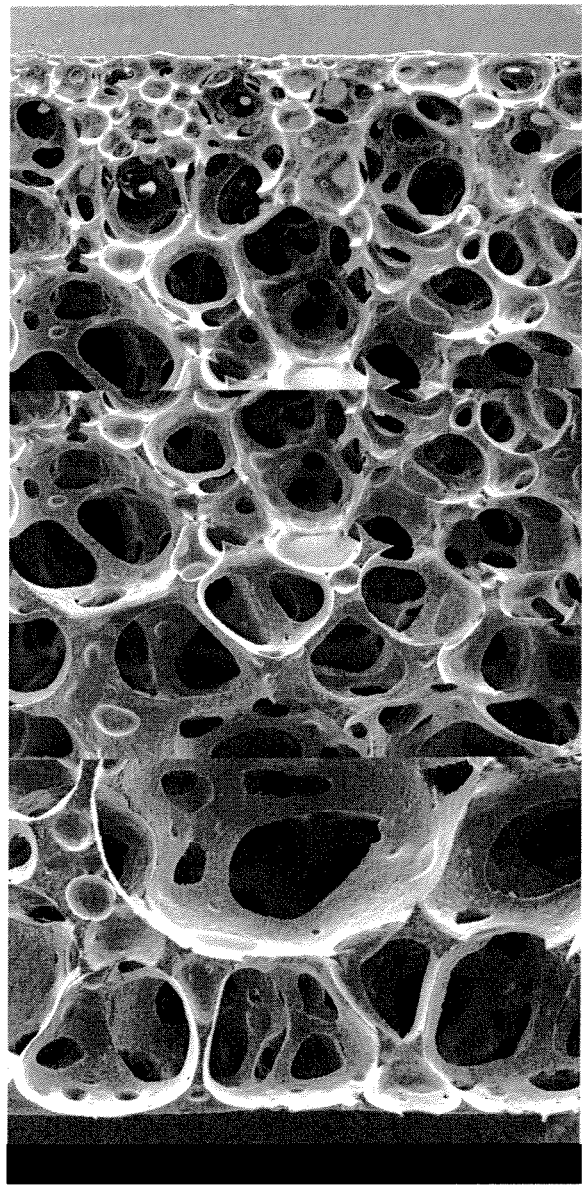
FIG. 6 is a Super-imposed Cross-Sectional SEM Images of Top-Middle-Bottom Regions of a porous dissolvable solid substrate.

| Example | Kr BET Surface Area (m$^2$/g) | Pycnometry % Open Cells | Micro-CT Cell Wall thickness (mm) | Micro-CT Star Volume (mm$^3$) | Micro-CT SMI Index | SEM Image | μCT Image |
|---|---|---|---|---|---|---|---|
| Ex. 1 | 0.036 | 89.1% | 0.074 | 5.1 | 1.5 | FIG. 5 | FIG. 6 |

The above data and referenced images demonstrate the dissolving porous solid shampoo of Example 1 to be predominantly open-celled and to have good physical integrity. Correspondingly, the predominantly open-celled dissolving porous shampoo solid also exhibits fast dissolution performance (6 to 8 strokes) within the simulated hand dissolution protocol as described herein.

Example 3

Porous Dissolvable Solid Shampoo Substrate with a Surface-Coated Starch Perfume Complex Comprising 50.1% of a Perfume 1a A starch perfume complex of a perfume 1a was obtained from Akzo Nobel (10 Finderne Ave., Bridgewater N.J. 07080) under the code EXP 5594. The perfume 1a was reported by the supplier to be complexed with a modified starch at approximately 50.1% by weight of the complex via a spray drying process and the resulting complex was in the form of a free flowing fine powder.

A porous dissolvable solid shampoo substrate from example 1 (and corresponding weigh boat) is removed from the sealed plastic bag and tared on a 4 place weigh balance. The starch perfume complex of a perfume 1a is then applied to the surface of each substrate. The substrate is coated with the starch perfume complex powder by gently shaking the substrate in a tray (or other suitable container) containing an excess of the starch perfume complex in a side-to-side manner ten times (the process is repeated for the other side). The resulting powder coated substrate is then picked up (with gloved hands) and gently shaken and tapped several times to remove any excess powder that is not sufficiently adhered to the substrate. The resulting weight of the modified starch perfume complex of the perfume 1a applied is recorded in the below table. The substrate within its weigh boat is then returned the zip lock bag and sealed from the atmosphere. This powder application process is repeated for the remaining substrates.

The final weights achieved are given in the below Table 4:

TABLE 4

| Substrate No. | Initial substrate weight | Weight of starch perfume complex of a perfume 1a applied |
|---|---|---|
| 1 | 1.091 | 0.191 |
| 2 | 1.060 | 0.181 |
| 3 | 1.141 | 0.147 |
| 4 | 1.073 | 0.139 |
| 5 | 1.227 | 0.197 |
| 6 | 1.225 | 0.197 |
| 7 | 1.156 | 0.150 |
| Average | 1.139 | 0.172 |
| Standard Deviation | 0.069 | 0.025 |

Example 4

Dissolving Porous Dissolvable Solid Shampoo Substrate with a Surface-Coated Starch Perfume Complex Comprising 53.9% of a Perfume 1a A starch perfume complex of a perfume 1a was obtained from Akzo Nobel (10 Finderne Ave., Bridgewater N.J. 07080) under the code EXP 5595. The perfume 1a was reported by the supplier to be complexed with a modified starch at approximately 53.9% by weight of the complex via a spray drying process and the resulting complex was in the form of a free flowing fine powder.

The porous dissolvable substrates are prepared according to the identical formulation and procedures as described in Example 3, but with the replacement of the starch perfume complex comprising 50.1% of perfume 1a with a different starch perfume complex comprising 53.9% of perfume 1a.

The final weights achieved are given in the below Table 5:

TABLE 5

| Substrate No. | Initial substrate weight | Weight of starchstarch perfume complex of a perfume 1a applied |
|---|---|---|
| 1 | 1.229 | 0.187 |
| 2 | 1.230 | 0.165 |
| 3 | 1.043 | 0.130 |
| 4 | 1.182 | 0.175 |
| 5 | 1.184 | 0.125 |
| 6 | 1.189 | 0.162 |
| 7 | 1.101 | 0.144 |
| Average | 1.165 | 0.155 |
| Standard Deviation | 0.069 | 0.023 |

Example 5

Dissolving Porous Dissolvable Solid Shampoo Substrate with a Surface-Coated Starchstarch Perfume Complex Comprising 51.9% of a Perfume 1b A starchstarch perfume complex of a perfume 1b was obtained from Akzo Nobel (10 Finderne Ave., Bridgewater N.J. 07080) under the code EXP 5596. The perfume 1b was reported by the supplier to be complexed with a starch at approximately 51.9% by weight of the complex via a spray drying process and the resulting complex was in the form of a free flowing fine powder.

The porous dissolvable substrates are prepared according to the identical formulation and procedures as described in Example 3, but with the replacement of the starch perfume complex comprising 50.1% of perfume 1a with a different starch perfume complex comprising 51.9% of perfume 1b. The final weights achieved are given below in Table 6:

TABLE 6

| Substrate No. | Initial Porous Dissolvable Solid Substrate weight | Weight of starch perfume complex of a perfume 1b applied |
|---|---|---|
| 1 | 1.176 | 0.130 |
| 2 | 1.214 | 0.145 |
| 3 | 1.095 | 0.155 |
| 4 | 1.128 | 0.145 |
| 5 | 1.079 | 0.156 |
| 6 | 1.197 | 0.155 |
| 7 | 1.208 | 0.187 |
| Average | 1.157 | 0.153 |
| Standard Deviation | 0.056 | 0.018 |

Example 6

Porous Dissolvable Solid Shampoo Substrate with a Surface-Coated Starch Perfume Complex Comprising 56.6% of a Perfume 1b A starch perfume complex of a perfume 1b was obtained from Akzo Nobel (10 Finderne Ave., Bridgewater N.J. 07080) under the code EXP 5597. The perfume 1b was reported by the supplier to be complexed with a starch at approximately 56.6% by weight of the complex via a spray drying process and the resulting complex was in the form of a free flowing fine powder.

The Porous Dissolvable Solid Shampoo Substrate are prepared according to the identical formulation and procedures as described in Example 3, but with a coating comprising the replacement of the starch perfume complex comprising 50.1% of perfume 1a with a different starch perfume complex comprising 56.6% of perfume 1b.

The final weights achieved are below in Table 7:

TABLE 7

| Substrate No. | Initial Porous Dissolvable Solid Substrate weight | Weight of starchstarch perfume complex of a perfume 1b applied |
| --- | --- | --- |
| 1 | 1.161 | 0.171 |
| 2 | 1.110 | 0.148 |
| 3 | 1.068 | 0.136 |
| 4 | 1.166 | 0.139 |
| 5 | 1.102 | 0.155 |
| 6 | 1.983 | 0.156 |
| 7 | 1.168 | 0.157 |
| Average | 1.251142857 | 0.151714286 |
| Standard Deviation | 0.324963808 | 0.011912379 |

Example 7

Porous Dissolvable Solid Shampoo Substrate with a Surface Coating of Aminosilicone, a Surface Coating of Perfume 1c, a Surface-Coated Starch Perfume Complex of a Secondary Perfume 2a, and a Surface-Coated Calcium Silicate Complex of a Secondary Perfume 2a A Porous Dissolvable Solid Shampoo Substrate from example 1 (and corresponding weigh boat) is removed from the sealed plastic bag and tared on a 4 place weigh balance. 65 microliters of aminosilicone fluid (available from Momentive, Performance Materials, Albany N.Y., Product code 65850Y-14945 with a viscosity of 14,500 cps at 25° C. and an amine content of 0.050 meq/g) is coated onto the top surface of the substrate (the side exposed to the atmosphere during the drying process and opposite the side in contact with the aluminum mold during production) with a positive displace micro-dispenser with a glass tube and plunger. The aminosilicone fluid is dispensed by placing five drops (about ⅕ the total volume each) on five spots (center and four corners on substrate). The side of the glass tube is used to distribute the aminosilicone fluid across the top surface of the substrate as evenly as possible. The weigh boat is returned to the scale and the weight of aminosilicone fluid added is recorded. The average weight of aminosilicone fluid applied across 14 different substrates used in this study was 0.060 grams with a standard deviation of 0.003 grams.

The first substrate within it's weigh boat is later (after several hours) removed from the zip-lock bag and tared again on a 4 place weigh balance. Within a fume hood, the Porous Dissolvable Solid Shampoo Substrate is mounted on a stainless steel easel that rests at about a 60 degree angle and with notches holding the substrate from sliding downward and with a hole in plate so that the substrate can easily be removed from the mount by pushing from the back of the easel. It is important that the top surface of the substrate (the side that was exposed to the air in the drying oven and opposite the side that was in direct contact with the aluminum mold during the drying process) is facing away from the easel. A small glass bottle with a pump spray is filled with the perfume oil 1c (the same perfume oil as perfume 1c referenced in the examples) and then sprayed onto the surface of the solid from a distance of 2 to 3 inches. The solid is then removed from the easel and returned to the weigh boat on the balance with the top side facing upwards. The weight of perfume applied is recorded and in the instance that the target weight is not achieved, either another spray amount is applied or a Kim wipe to absorb excess perfume away from the substrate. This iterative process is repeated until the target weight range is achieved. The target amount of perfume 1c applied was 0.06 grams. The resulting substrate resting on the small weigh boat is stored within a zip-lock bag and sealed from the atmosphere. The above process is repeated on subsequent substrates from Example 1.

The preparation of a calcium silicate complex of a secondary perfume 2a is prepared with the use of a Flacktek Speemixer™ DAC400FV (By HAUSCHILD, Waterkamp 1, 509075 Hamm, Germany) and a four place weigh balance. 5 grams of calcium silicate (Hubersorb 600 supplied by Huber Engineered Materials, Havre de Grace, Md. and reported by the supplier to have an oil absorption of 475 cc/100 g, an average particle size of 6 microns, a BET surface area of 300 $m^2/g$ and a bulk density of 8 lbs/CFT) is weighed into a Flacktek Speedmixer 60 max jar. 5 grams of the secondary perfume oil 2a is then weighed into the same 60 max jar with the use of a pipette. The jar is then sealed shut with the corresponding lid and speedmixed for approximately 60 seconds at 2750 rpm. The high impact perfume accord 2a is accordingly complexed at approximately 50% by weight of the complex and with the resulting complex in the form of a free flowing fine powder.

A starch perfume complex of a secondary perfume 2a was obtained from Akzo Nobel (10 Finderne Ave., Bridgewater N.J. 07080) under the code EXP 5676. The perfume 1a was reported by the supplier to be complexed with a starch at approximately 41.3% by weight of the complex via a spray drying process and the resulting complex was in the form of a free flowing fine powder.

The calcium silicate complex of secondary perfume 2a and starch perfume complex of secondary perfume 2a are blended together with the use of the Flacktek Speemixer™ DAC400FV at a weight ratio of 30 to 70 of the former in relation to the latter. 0.6 grams of the calcium silicate perfume complex and 1.4 grams of the starch perfume complex is weighed into a Flacktek Speedmixer 60 max jar. The jar is then sealed shut with the corresponding lid and speedmixed for approximately 35 seconds at 2750 rpm. The weight percentage of the high impact perfume accord 2a in the resulting blended powder is approximately 43.9% by weight of the combined powders and with the resulting powder blend being in the form of a free flowing fine powder.

The powder blend is applied to the substrates according to the same procedure as described in Example 3, but with the replacement of the starch perfume complex comprising 53.9% of perfume 1a with the above powder blend of the calcium silicate complex of secondary perfume 2a and starch perfume complex of secondary perfume 2a. A substrate is loaded with 0.151 grams of the powder blend for Expert Perfume Sensory Panel Evaluation.

Expert Perfume Sensory Panel Evaluations

Table 8 summarizes Expert Perfume Sensory Panel data comparing the porous dissolvable solid substrate from examples 3, 4, 5 and 6 comprising surface resident coatings of differing starch perfume complexes of primary perfumes 1a and 1b to the retail Herbal Essences Drama Clean liquid shampoo product control. The data was collected by the method as described herein.

TABLE 8

| | | | | | | | |
|---|---|---|---|---|---|---|---|
| | | | | INTENSITY SCALE 1-100 (No odor-most intense possible) | | | |
| Products | Neat Product Odor | Bloom (In hand) | Lather (On switch) | Wet | 4 Hr (Damp) | 24 hr | 24 hr (Rewet/comb) |
| Herbal Essences Drama Clean shampoo reference Production code (L)71525395TA) | Peachy fruity citrus | 75 | 80 Peachy fruity citrus | 40 Peachy musky | 30 | 15/20 | 15 |
| Example 3: Dissolving porous solid shampoo with a surface-coated starch perfume complex comprising 50.1% of a perfume 1a | Peachy green aldehydic | 80 Nice | 80 | 55 Peachy | 40/45 | 20/25 | 15/20 |
| Example 4: Dissolving porous solid shampoo with a surface-coated starch perfume complex comprising 53.9% of a perfume 1a | Peachy green aldehydic | 75 | 70/75 | 50 Aldehydic | 40 | 20 | 15/20 |
| Example 5: Dissolving porous solid shampoo with a surface-coated starch perfume complex comprising 51.9% of a perfume 1b | Fruity green citrus aldehydic | 75/80 | 80 | 50 Citrusy | 40 | 25 Blooming Mango | 15/20 |
| Example 6: Dissolving porous solid shampoo with a surface-coated starch perfume complex comprising 56.6% of a perfume 1b | Fruity green citrus aldehydic | 80 | 80 | 50 Citrusy | 40 | 20/25 | 15/20 |

The above data demonstrates that the porous dissolvable solid substrate shampoos with surface resident coatings comprising starch perfume complexes of the present invention to provide improved panel perceptible perfume longevity on hair at the wet, 4 hour and 24 hour time points relative to the retail Herbal Essences Drama Clean liquid shampoo control product.

Table 9 summarizes Expert Perfume Sensory Panel data comparting the porous dissolvable solid substrate with a surface coating of aminosilicone, a surface coating of perfume 1c, a surface-coated starchstarch perfume complex of a secondary perfume 2a, and a surface-coated calcium silicate complex of a secondary perfume 2a from Example 7 to the retail Herbal Essences Drama Clean liquid shampoo product control. The data was collected by the method as described herein.

TABLE 9

| | | | | INTENSITY SCALE 1-100 (No odor-most intense possible) | | | | |
|---|---|---|---|---|---|---|---|---|
| Products | Neat Product Odor | Bloom (In hand) | Lather (On switch) | Wet | 7 Hr (sl. damp) | 24 hr | 48 hr | 48 hr (Rewet/comb) |
| Herbal Essences Drama Clean shampoo reference | Peachy citrus | 75/80 | 75/80 | 45/50 Peachy | 30 | 10 | 5 | 5 |
| Example 7: Dissolving porous solid shampoo with a surface coating of aminosilicone, a surface coating of perfume 1c, a surface-coated starch perfume complex of a secondary perfume 2a, and a surface-coated calcium silicate complex of a secondary perfume 2a | Green floral | 80 Rosy green | 80 | 65/70 Rosy | 60/65 | 20/25 Green floral | 5/10 | 25/30 Green floral |

The above data demonstrates that the porous dissolvable solid substrate with a surface coating of aminosilicone, a surface coating of perfume 1c, a surface-coated starch perfume complex of a secondary perfume 2a, and a surface-coated calcium silicate complex of a secondary perfume 2a of the present invention to provide improved panel perceptible perfume longevity on hair at the wet, 7 hours, 24 hours and 48 hour time points relative to the retail Herbal Essences Drama Clean liquid shampoo control product.

Note that any actives and/or compositions disclosed herein can be used in and/or with the articles, and in particular the household care articles, disclosed in the following U.S. patent applications, including any publications claiming priority thereto: U.S. 61/229,981; U.S. 61/229,986; U.S. 61/229,990; U.S. 61/229,996; U.S. 61/230,000; and U.S. 61/230,004. Such articles may comprise one or more of the following: detersive surfactant; plasticizer; enzyme; suds suppressor; suds booster; bleach; bleach stabilizer; chelant; cleaning solvent; hydrotrope; divalent ion; fabric softener additive (e.g. quaternary ammonium compounds); nonionic surfactant; perfume; and/or a perfume delivery system. Such articles may be utilized in methods including, but not limited to: dosing into a washing machine to clean and/or treat fabric; dosing into a dishwasher to clean and/or treat cutlery; and dosing into water to clean and/or treat fabric and/or hard surfaces.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making a personal care article, the method comprising applying a surface resident coating comprising a starch perfume complex in powdered form to a porous dissolvable solid substrate comprising from about 10% to about 75% by weight of the personal care article of a surfactant, from about 10% to about 50% by weight of the personal care article of a water-soluble polymer, and from about 1% to about 30% by weight of the personal care article of a plasticizer, wherein the porous dissolvable solid substrate comprises a percent open cell content from about 80% to about 100.0%.

2. A method for making a personal care article, the method comprising:
    (a) preparing a processing mixture comprising from about 5% to about 50% by weight of the personal care article of a surfactant, from about 5% to about 35% by weight of the personal care article of a water-soluble polymer, and from about 0.5% to about 20% by weight of the personal care article of a plasticizer;
    (b) aerating the processing mixture by introducing a gas into the processing mixture to form an aerated wet mixture;
    (c) forming the aerated wet mixture into one or more desired shapes;
    (d) drying the aerated wet mixture to form a porous dissolvable solid substrate having a percent open cell content from about 80% to about 100.0%; and
    (e) applying a surface resident coating comprising a starch perfume complex in powdered form to the porous dissolvable solid substrate.

3. The method of making a personal care article according to claim 2, wherein the surface resident coating comprising the starch perfume complex is applied to the porous dissolvable solid substrate at a humidity of about 20% to about 70%.

4. The method of making a personal care article according to claim 2, wherein the surface resident coating comprising the starch perfume complex is applied to the porous dissolvable solid substrate at a humidity of about 30% to about 60%.

5. The method of making a personal care article according to claim 2, wherein the surface resident coating comprising the starch perfume complex is applied to the porous dissolvable solid substrate having a moisture content of about 5% to about 20%.

* * * * *